US005298631A

United States Patent [19]

Sanda et al.

[11] Patent Number: 5,298,631

[45] Date of Patent: Mar. 29, 1994

[54] SPIROORTHOCARBONATE COMPOUND AND COPOLYMERS OBTAINED THEREFROM

[75] Inventors: Fumio Sanda, Okayama; Junichi Yamauchi, Kurashiki; Toshikazu Takata; Takeshi Endo, both of Yokohama, all of Japan

[73] Assignee: Kuraray Co., Ltd., Kurashiki, Japan

[21] Appl. No.: 850,274

[22] Filed: Mar. 12, 1992

[30] Foreign Application Priority Data

| | | | |
|---|---|---|---|
| Mar. 12, 1991 | [JP] | Japan | 3-741541 |
| Mar. 12, 1991 | [JP] | Japan | 3-741551 |
| May 2, 1991 | [JP] | Japan | 3-130609 |
| Aug. 2, 1991 | [JP] | Japan | 3-217998 |
| Nov. 1, 1991 | [JP] | Japan | 3-315529 |

[51] Int. Cl.[5] .......... C07D 321/10

[52] U.S. Cl. .......... 549/334; 526/204; 526/206; 523/116; 260/998.11

[58] Field of Search .......... 549/334; 526/204, 206; 523/116

[56] References Cited

U.S. PATENT DOCUMENTS

| | | | |
|---|---|---|---|
| 4,089,763 | 5/1978 | Dart et al. | 204/159.23 |
| 4,110,184 | 8/1978 | Dart et al. | 204/159.23 |

FOREIGN PATENT DOCUMENTS

| | | |
|---|---|---|
| 55-33687 | 9/1980 | Japan . |
| 56-152408 | 11/1981 | Japan . |
| 2074590 | 11/1981 | United Kingdom . |

OTHER PUBLICATIONS

Sanda et al., Chem. Abst. 118-102888t (1993).

Journal of Polymer Science, Polymer Letters Edition, vol. 13, 1975, pp. 193-195, T. Endo, et al., "Radical Ring-Opening Polymerization of 3,9-Dimethylene-1,5,7,11-Tetraoxaspiro-(5,5)Undecane".

Journal of Polymer Science, Part A: Polymer Chemistry, vol. 27, No. 4, Mar. 1989, pp. 1415-1418, H. Tagoshi, et al., "Radical Polymerization of Unsaturated Spiroorthocarbonate".

Chemical Abstracts, vol. 108, No. 20, May 16, 1988, No. 168067z, T. Takata, et al., "New Aspect of Cationic Ring-Opening Polymerization of Seven-Membered Spiroorthocarbonates: Synthesis and . . . ".

Chemical Abstracts, vol. 110, No. 19, May 8, 1989, No. 173203m, K. No, et al., "The Synthesis of Spiro Orthocarbonates".

Journal of Polymer Science, Polymer Chemistry Edition, vol. 25, No. 10, pp. 2925-2929, Oct., 1987, T. Endo, et al., "Preparation of Polymerization of Spiroorthocarbonate Containing Distyryl Structure".

*Primary Examiner*—Cecilia Tsang

*Attorney, Agent, or Firm*—Oblon, Spivak, McClelland, Maier & Neustadt

[57] ABSTRACT

An asymmetric spiroorthocarbonate compound having one exomethylene group and represented by the following general formula (1)

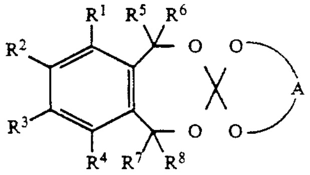

(1)

wherein A represents a group selected from the group consisting of:

and

-continued

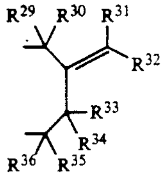

wherein $R^1$, $R^2$, $R^3$ and $R^4$ each represents a hydrogen atom, a lower alkyl group having not more than 8 carbon atoms, an alkoxy group, a halogen group, a nitro group, a cyano group, an amino group, an amide group, a hydroxyl group or an alkyl ester group having not more than 20 carbon atoms; and $R^5$, $R^6$, $R^7$ and $R^8$, $R^9$ through $R^{14}$, $R^{15}$ through $R^{22}$, $R^{23}$ through $R^{28}$ and $R^{29}$ through $R^{36}$ each represents a hydrogen atom or a lower alkyl group having not more than 8 carbon atoms; and copolymers containing units therefrom.

7 Claims, 20 Drawing Sheets

SPIROORTHOCARBONATE COMPOUND AND COPOLYMERS OBTAINED THEREFROM

BACKGROUND OF THE INVENTION

Field of the Invention

The present invention relates to novel spiroothocarbonate compounds and also to copolymers containing them as one of the components. The compounds and copolymers of the present invention are novel and usable for molding materials, composite materials, injection materials, sealing materials, medical and dental materials, paints, adhesives and like materials.

It is well known that polymerizable monomers such as acrylonitrile, vinyl acetate, methyl methacrylate, styrene, ethylene oxide and epichlorohydrin shrink to a large extent upon polymerization. Shrinkage in volume of thermosetting resins such as epoxy and phenol resins upon curing causes a large trouble in the fields of injection molding, sealant application, adhesive application and the like.

A material undergoing no shrinkage upon polymerization would realize precise molding due to improvement in dimensional accuracy and minimization of clearance generation and increase the strength or adhesiveness of finished articles thanks to reduction of internal stress.

Spiroorthocarbonates are known monomers that exhibit expansion in volume upon polymerization. Ring-opening polymerization of spiroothocarbonates are generally conducted by cationic polymerization with a Lewis acid such as borontrifluoride ether complex. Some end-uses, however, favor a system where the ring-opening polymerization is effected by radical polymerization with accompanying volume expansion occurs.

Spiroorthocarbonates having exomethylene group are useful monomers, which polymerize, reportedly, not only by cationic polymerization but also by radical polymerization to yield polymers.

It has also been reported that spiroothocarbonates having an exomethylene group at the α-position of its ether oxygen and consisting of two 5-membered rings ("1" shown below) undergo only vinyl polymerization upon radical polymerization, to yield crosslinked polymers [H. Tagoshi and Endo, J. Polym. Sci., Chem. Ed., 27, 1415 (1989)].

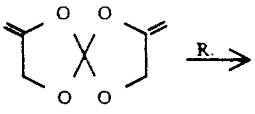

1

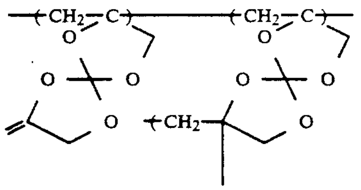

Further it has been reported that spiroorthocarbonates having exomethylene group at the β-position of its ether oxygen and consisting of two 6-membered rings ("2" shown below) undergo ring-opening isomerization upon solution radical polymerization, to yield polyether carbonates [T. Endo and W. J. Bailey, J. Polym. Sci., Polym. Lett. Ed., 13, 193 (1975)]

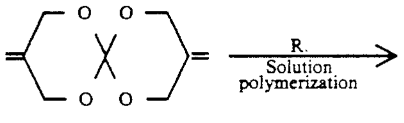

2

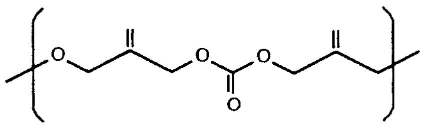

2 R. Bulk polymerization Crosslinked polymer

The compound shown by 2, however, has the problem of yielding a crosslinked polymer upon bulk radical polymerization, thereby exhibiting a small expansion on polymerization.

SUMMARY OF THE INVENTION

Accordingly, an object of the present invention is to provide a spiroorthocarbonate compound that will, upon radical polymerization, undergo ring-opening isomerization polymerization and exhibit large expansion in volume upon polymerization.

Another object of the present invention is to provide a copolymer having a component of the above spiroorthocarbonate compound.

The present inventors considered that it is important for the desired compound to have the following features with respect to its structure. For the purpose of undergoing radical polymerization, the compound should have an exomethylene group to which the radical can add. If, however, the resulting polymer has some remaining exomethylene groups, crosslinking will proceed so that the polymer that has undergone ring-opening polymerization and expanded may again shrink. It is therefore necessary and sufficient, for addition of the radical, that only one exomethylene group be present, thus excluding unnecessary exomethylene groups, in the molecule of the compound. Consequently, the compound desirably has an asymmetric spiroorthocarbonate structure.

Presence of an exomethylene group in the molecule necessarily leads to occurrence of, in addition to ring-opening polymerization, the side reaction of vinyl polymerization. For the purpose of permitting ring-opening polymerization to proceed in preference to vinyl polymerization, the following two points were considered to be important.

(1) The spiro ring has strain and is hence readily openable; and (2) The compound forms, upon opening polymerization, a stable propagating radical end unit, such as benzyl radical, allyl radical or the like.

The present inventors synthesized various asymmetric spiroorthocarbonate compounds having exomethylene group at the α-position of the ether oxygen and those having exomethylene group at the β-position of the ether oxygen, and have studied on their radical polymerization behavior to find that such spiroorthocarbonate compounds as provided by the present invention does not undergo crosslinking reaction upon bulk radical polymerization and develops, thereupon, expansion in volume.

Thus, the present invention provides an asymmetric spiroorthocarbonate compound having only one exomethylene group and represented by the following general formula (1)

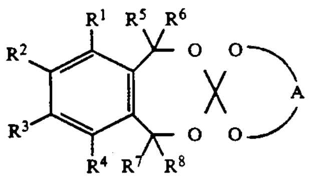

(1)

wherein A represents a group selected from the group consisting of:

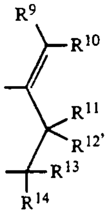

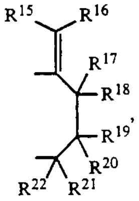

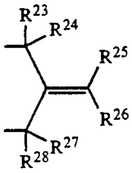

and

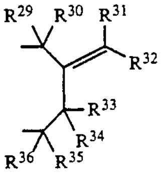

wherein $R^1$, $R^2$, $R^3$ and $R^4$ each represents a hydrogen atom, a lower alkyl group having not more than 8 carbon atoms, an alkoxy group, a halogen group, a nitro group, a cyano group, an amino group, an amide group, a hydroxyl group or an alkyl ester group having not more than 20 carbon atoms; and $R^5$, $R^6$, $R^7$ and $R^8$, $R^9$ through $R^{14}$, $R^{15}$ through $R^{22}$, $R^{23}$ through $R^{28}$ and $R^{29}$ through $R^{36}$ each represents a hydrogen atom or a lower alkyl group having not more than 8 carbon atoms.

The present-invention also provides a copolymer having the component of the above spiroorthocarbonate compound represented by the formula (1).

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
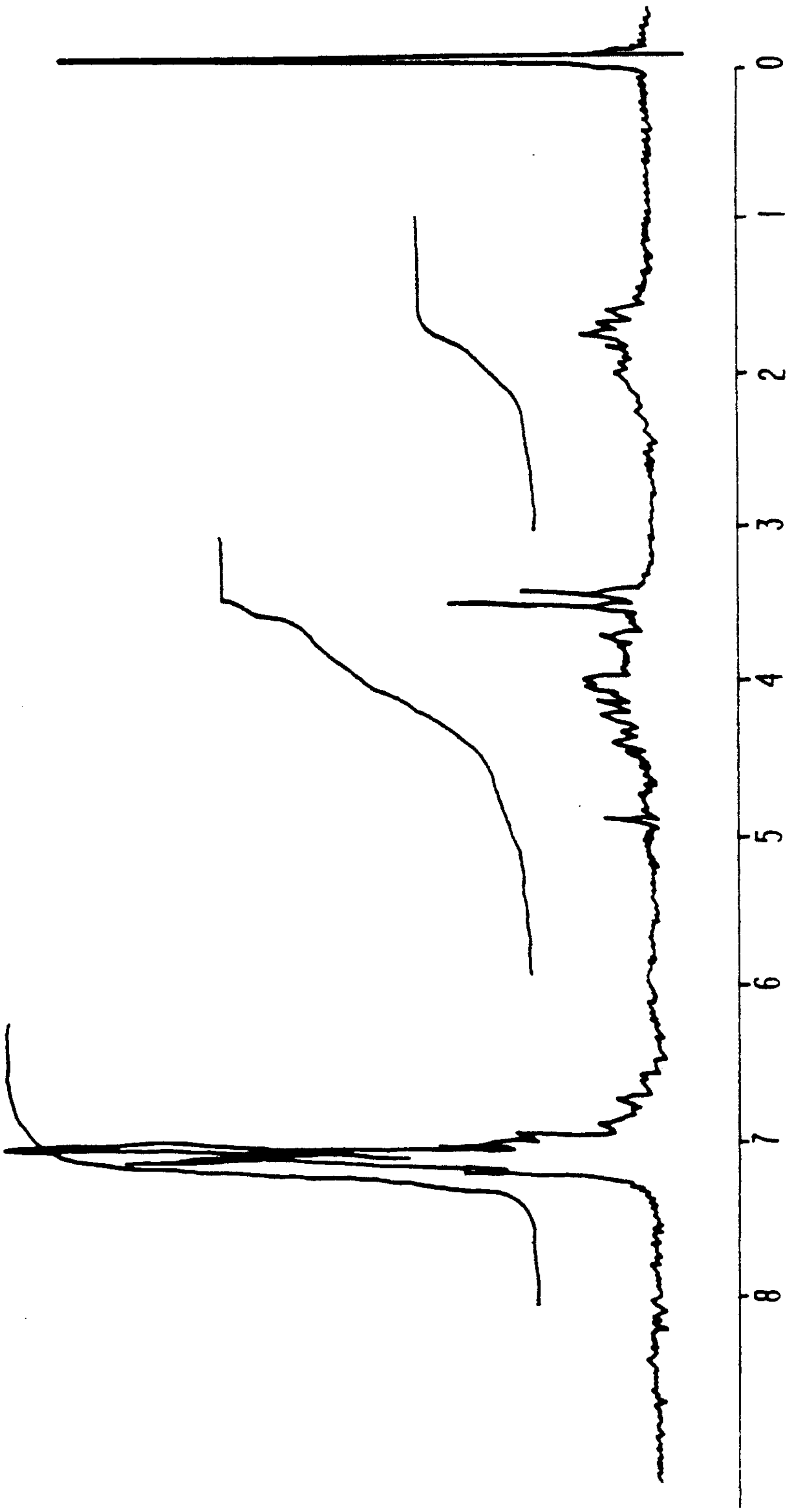
FIGS. 1 and 3 show $^1$H-NMR spectra of the dioxane and spirodioxane produced as intermediates in Examples 1, respectively.

The spiroorthocarbonate compounds of the present invention are described hereunder. The spiroorthocarbonate compounds having an exomethylene group at the α-position of the ether oxygen include the following two types.

The first type is the compound of the formula (1) with

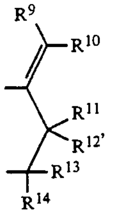

i.e.

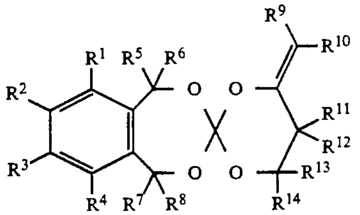

(2)

wherein $R^1$, $R^2$, $R^3$ and $R^4$ each represents a hydrogen atom, a lower alkyl group having not more than 8 carbon atoms, an alkoxy group, a halogen group, a nitro group, a cyano group, an amino group, an amide group, a hydroxyl group or an alkyl ester group having not more than 20 carbon atoms; and $R^5$, $R^6$, $R^7$, $R^8$, $R^9$, $R^{10}$, $R^{11}$, $R^{12}$, $R^{13}$ and $R^{14}$ each represents a hydrogen atom or a lower alkyl group having not more than 8 carbon atoms.

Examples of the lower alkyl group having not more than 8 carbon atoms which may be represented by each of $R^1$, $R^2$, $R^3$ and $R^4$ are methyl, ethyl, n-propyl, i-propyl, n-butyl, i-butyl, tert-butyl, n-pentyl, n-hexyl, n-heptyl and n-octyl; examples of the alkoxy group are methoxy, ethoxy, n-propoxy, i-propoxy, n-butoxy and n-pentoxy; examples of the halogen group are chloro and bromo; examples of the amino group are N-methylamino and N,N-dimethylamino; examples of the amide group are aminocarbonyl and formylamino; and examples of the alkyl ester group having not more than 20 carbon atoms are methoxycarbonyl, propoxycarbonyl and acetoxy. Examples of the lower alkyl group having not more than 8 carbon atoms which may be represented by each of $R^5$, $R^6$, $R^7$, $R^8$, $R^9$, $R^{10}$, $R^{11}$, $R^{12}$, $R^{13}$ and $R^{14}$ are methyl, ethyl, n-propyl, i-propyl, n-butyl, i-butyl, tert-butyl, n-pentyl, n-hexyl, n-heptyl and n-octyl.

Concrete examples of the compound of the present invention are as follows.

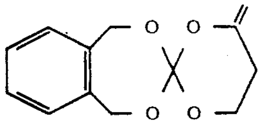

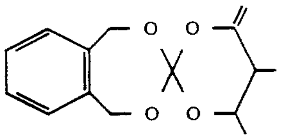

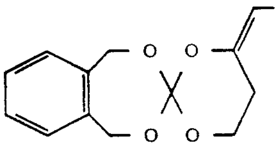

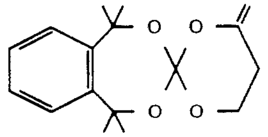

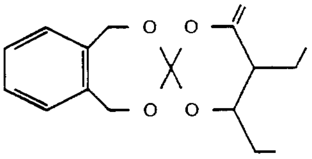

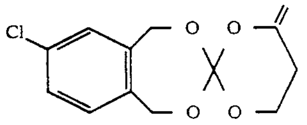

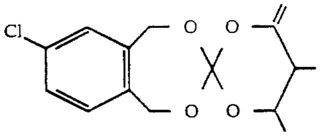

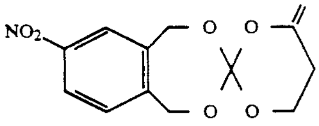

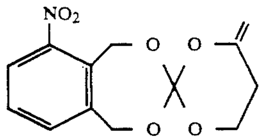

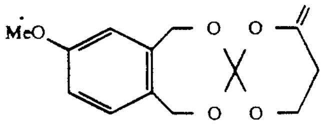

-continued

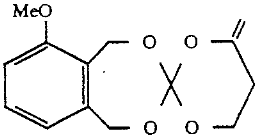

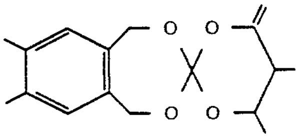

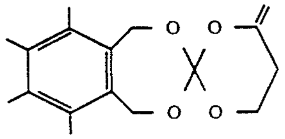

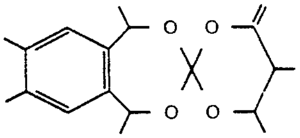

The spiroorthocarbonate compound represented by the formula (2) may be produced by any process and with no specific limitations. Examples of commercially advantageous production process are as follows.

A dihalodiaryloxymethane represented by the following formula (3)

(3)

wherein Ar and X represent an aromatic group and a halogen group respectively, and a diol represented by the following formula (4)

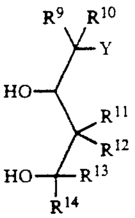

(4)

wherein $R^9$, $R^{10}$, $R^{11}$, $R^{12}$, $R^{13}$ and $R^{14}$ each represents a hydrogen atom or a lower alkyl group having not more than 8 carbon atoms and Y represents a halogen group, are dehydrohalogenated to yield a dioxane represented by the following formula (5)

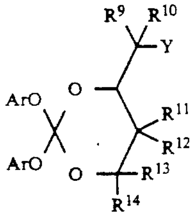

(5)

wherein Ar represents an aromatic group, $R^9$, $R^{10}$, $R^{11}$, $R^{12}$, $R^{13}$ and $R^{14}$ each represents a hydrogen atom or a lower alkyl group having not more than 8 carbon atoms, and Y represents a halogen group.

The dioxane thus obtained and a diol represented by the following formula (6)

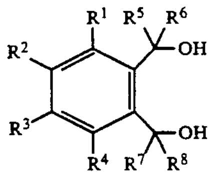

(6)

wherein $R^1$, $R^2$, $R^3$ and $R^4$ each represents a hydrogen atom, a lower alkyl group having not more than 8 carbon atoms, an alkoxy group, a halogen group, a nitro group, a cyano group, an amino group, an amide group, a hydroxyl group and an alkyl ester group having not more than 20 carbon atoms, and $R^5$, $R^6$, $R^7$ and $R^8$ each represents a hydrogen atom or a lower alkyl group having not more than 8 carbon atoms, are then subjected to dearylol reaction, to yield a spiroorthocarbonate compound represented by the following formula (7)

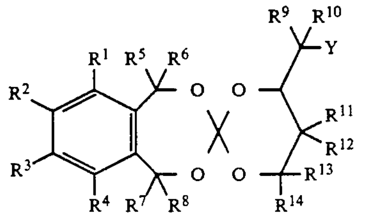

(7)

wherein $R^1$, $R^2$, $R^3$ and $R^4$ each represents a hydrogen atom, a lower alkyl group having not more than 8 carbon atoms, an alkoxy group, a halogen group, a nitro group, a cyano group, an amide group, a hydroxyl group or an alkyl ester group having not more than 20 carbon atoms; Y represents a halogen group and $R^5$, $R^6$, $R^7$, $R^8$, $R^9$, $R^{10}$, $R^{11}$, $R^{12}$, $R^{13}$ and $R^{14}$ each represents a hydrogen atom or a lower alkyl group having not more than 8 carbon atoms. The obtained spiroorthocarbonate compound is dehydrohalogenated to give the desired spiroorthocarbonate compound represented by the formula (2).

An alternative and more preferred process is as follows. The dihalodiaryloxymethane represented by the formula (3) and the diol represented by the formula (6) are dehydrohalogenated to Yield a dioxepane represented by the following formula (8)

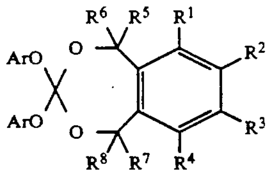

(8)

wherein Ar represents an aromatic group; $R^1$, $R^2$, $R^3$ and $R^4$ each represents a hydrogen atom, a lower alkyl group having not more than 8 carbon atoms, an alkoxy group, a halogen group, a nitro group, a cyano group, an amino group, an amide group, a hydroxyl group or an alkyl ester group having not more than 20 carbon atoms; and $R^5$, $R^6$, $R^7$ and $R^8$ each represents a hydrogen atom or a lower alkyl group having not more than 8 carbon atoms. The obtained dioxepane and the diol represented by the formula (4) are subjected to dearylol reaction to yield the spiroorthocarbonate compound represented by the formula (7), which is then dehydrohalogenated to yield the spiroorthocarbonate compound represented by the formula (2).

Examples of the aromatic group represented by Ar in the dihalodiaryloxymethane represented by the above formula (3) are phenyl, p-methylphenyl, p-ethylphenyl, p-propylphenyl, p-phenylphenyl, 1-naphthyl and 2-naphthyl, and those of the halogen group represented by X are chloro, bromo and iodo.

Examples of the halogen group represented by Y in the diol represented by the above formula (4) are chloro, bromo and iodo.

The dehydrohalogenation reaction of the dihalodiaryloxymethane represented by the formula (3) and the diol represented by the formula (4) or formula (6) is conducted by mixing these two compounds in the presence of an amine such as trimethylamine, triethylamine or tri-n-propylamine. The two compounds are preferably mixed in equimolar quantities. The amine is used in an amount of 200 to 600% by mole based on the moles of the dihalodiaryloxymethane, preferably 200 to 300% by mole on the same basis.

The reaction is conducted at a temperature in a range of −78° to 100° C., preferably −20° to 50° C. and generally under an atmosphere of an inert gas such as nitrogen, argon or helium.

The reaction may be conducted in the absence of solvent but, preferably, in the presence of a solvent such as halohydrocarbon, e.g. methylene chloride, chloroform or tetrachloroethylene, because of ready removal of reaction heat and ready operability.

The reaction time is generally selected from a range from 1 to 100 hours. After the desired conversion ratio has been attained, the reaction mixture is washed with water and, then, the resultant dioxane represented by the formula (5) or dioxepane represented by the formula (8) is isolated and purified in the usual manner.

The dearylol reaction of the dioxane and the diol represented by the formula (6) or that of the dioxepane and the diol represented by the formula (4) is conducted by mixing the two compounds in the presence of an acid catalyst such as p-toluenesulfonic acid or benzenesulfonic acid. The two compounds are preferably mixed in equimolar quantities. The acid catalyst is added in an amount of 0.01 to 10% by mole based on the moles of the dioxane or dioxepane, preferably 0.1 to 5% by mole on the same basis.

The reaction is conducted at a temperature in a range of −78° to 100° C., preferably −20° to 50° C. and generally under an atmosphere of an inert gas such as nitrogen, argon or helium.

The reaction may be conducted in the absence of any solvent but, preferably, in the presence of a solvent such as halohydrocarbon, e.g. methylene chloride, chloroform or tetrachloroethylene, because of ready removal of reaction heat and ready operability.

The reaction time is generally selected from a range from 1 to 100 hours. After the desired conversion ratio has been attained, the reaction mixture is washed with water and, then, the resultant spiroorthocarbonate represented by the formula (7) is isolated and purified in the usual manner.

Dehydrohalogenation of the spiroorthocarbonate compound represented by the formula (7) is conducted by mixing the compound with a sodium or potassium alkoxide, such as sodium methoxide, potassium methoxide or potassium tert-butoxide. The sodium or potassium alkoxide is used in an amount of 100 to 200% by mole based on the moles of the spiroorthocarbonate compound, preferably 100 to 130% by mole on the same basis.

The reaction is conducted at a temperature in a range of −78° to 100° C., preferably −20° to 50° C. and generally under an atmosphere of an inert gas such as nitrogen, argon or helium.

The reaction may be conducted in the absence of any solvent but, preferably, in the presence of a solvent such as N,N-dimethylformamide, dimethyl sulfoxide or tetrahydrofuran, because of ready removal of reaction heat and ready operability.

The reaction time is generally selected from a range from 1 to 100 hours. After the desired conversion ratio has been attained, the reaction mixture is washed with water and, then, the desired spiroorthocarbonate is isolated and purified in the usual manner.

Another species of the spiroorthocarbonate compound of the present invention are those of the formula (1) and A

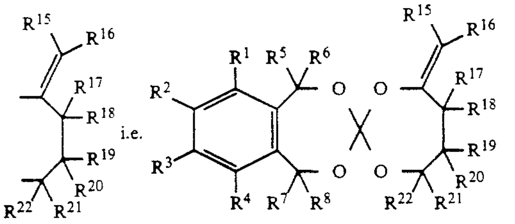
(9)

wherein $R^1$ through $R^8$ are as defined before, and $R^{15}$ through $R^{22}$ each represents a hydrogen atom or a lower alkyl group having not more than 8 carbon atoms.

Examples of the lower alkyl group which may be represented by each of $R^{15}$ through $R^{22}$ are those having not more than 8 carbon atoms, such as methyl, ethyl, n-propyl, i-propyl, n-butyl, i-butyl, tert-butyl, n-pentyl, n-hexyl, n-heptyl and n-octyl.

Concrete examples of the compound are as follows.

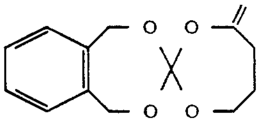

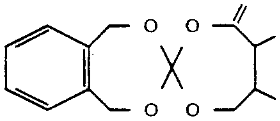

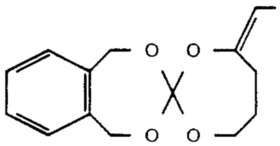

-continued

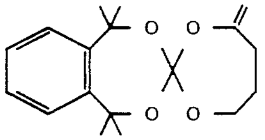

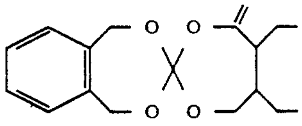

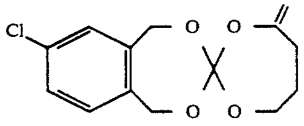

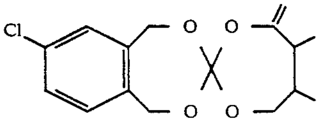

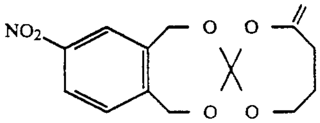

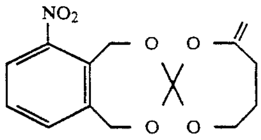

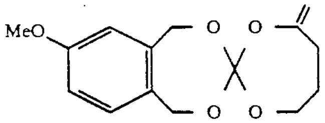

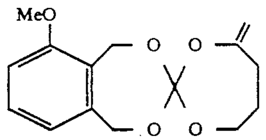

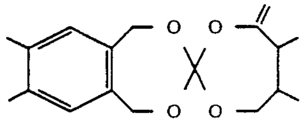

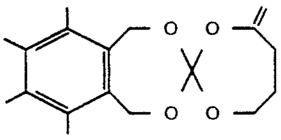

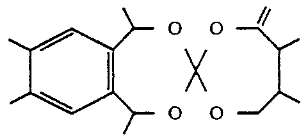

The spiroorthocarbonate compound represented by the formula (9) may be produced in the same manner as described for that represented by the formula (2) except for using, instead of a diol represented by the formula (4), one represented by the following formula (10)

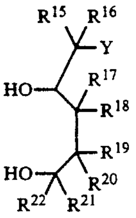
(10)

wherein $R^{15}$ through $R^{22}$ are as defined before and Y represents a halogan group.

The following two types of spiroorthocarbonate compounds having exomethylene group at the β-position of the ether oxygen are also included in the compound of the present invention. The first type is the compounds with A

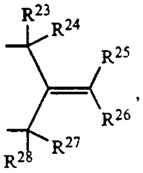
(11)

, i.e.

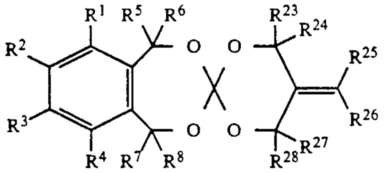

wherein $R^1$ through $R^8$ are as defined before, and $R^{23}$ through $R^{28}$ each represents a hydrogen atom or a lower alkyl group having not more than 8 carbon atoms.

Concrete examples of the compound represented by the formula (11) are as follows.

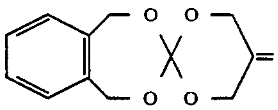

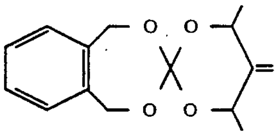

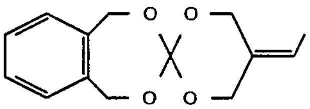

-continued

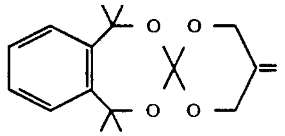

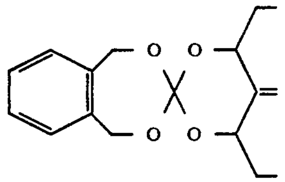

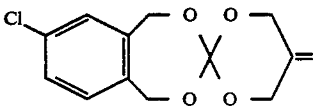

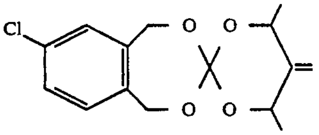

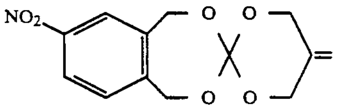

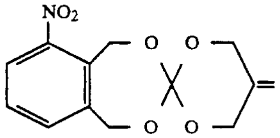

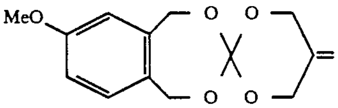

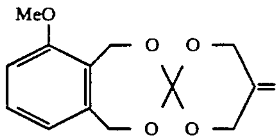

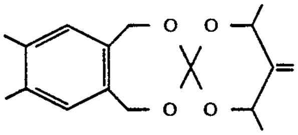

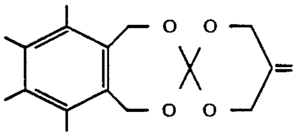

-continued

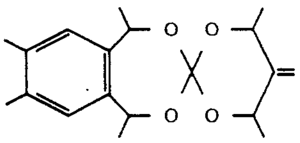

The spiroorthocarbonate compound represented by the formula (11) may be produced by any process with no specific limitations. An example of industrially advantageous processes for the production is as follows.

A dihalodiaryloxymethane represented by the following formula (12)

(12)

wherein Ar and X represent an aromatic group and a halogen group respectively, and a diol represented by the following formula (13)

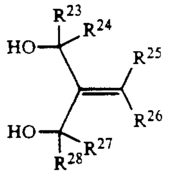
(13)

wherein $R^{23}$ through $R^{28}$ each represents a hydrogen atom or a lower alkyl group having not more than 8 carbon atoms, are dehydrohalogenated to yield a dioxane represented by the following formula (14)

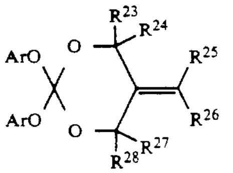
(14)

wherein $R^{23}$ through $R^{28}$ are as defined above.

The dioxane thus obtained and a diol represented by the following formula (6)

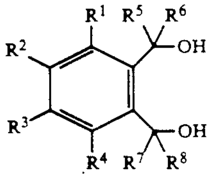
(6)

wherein $R^1$ through $R^8$ are as defined before, are then subjected to dearylol reaction, to yield a spiroorthocarbonate compound represented by the formula (11).

An alternative and more preferred process is as follows. The dihalodiaryloxymethane represented by the formula (12) and the diol represented by the formula (6) are dehydrohalogenated to yield a dioxepane represented by the following formula (15)

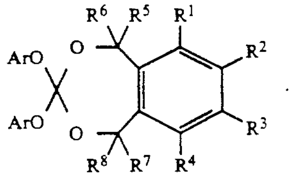
(15)

wherein $R^1$ through $R^8$ and Ar are as defined before.

The thus obtained dioxepane and the diol represented by the formula (13) are subjected to dearylol reaction to yield the spiroorthocarbonate compound represented by the formula (11).

Examples of the aromatic group represented by Ar in the dihalodiaryloxymethane represented by the formula (12) are phenyl, p-methylphenyl, p-ethylphenyl, p-propylphenyl, p-phenylphenyl, 1-naphthyl and 2-naphthyl, and those of the halogen group represented by X are chloro, bromo and iodo.

The dehydrohalogenation reaction of the above dihalodiaryloxymethane and diol is conducted by mixing these two compounds in the presence of an amine such as trimethylamine, triethylamine or tri-n-propylamine. The two compounds are preferably mixed in equimolar quantities. The amine is used in an amount of 100 to 300% by mole based on the moles of the dihalodiaryloxymethane, preferably 100 to 150% by mole on the same basis.

The reaction is conducted at a temperature in a range of $-78°$ to $100°$ C., preferably $-20°$ to $50°$ C. and generally under an atmosphere of ah inert gas such as nitrogen, argon or helium.

The reaction may be conducted in the absence of solvent but, preferably, in the presence of a solvent such as halohydrocarbon, e.g. methylene chloride, chloroform or tetrachloroethylene, because of ready removal of reaction heat and ready operability.

The reaction time is generally selected from a range from 1 to 100 hours. After the desired conversion ratio has been attained, the reaction mixture is washed with water and, then, the dioxane or dioxepane is isolated and purified.

The dearylol reaction of the dioxane and the diol or that of the dioxepane and the diol is conducted by mixing the two compounds in the presence of an acid catalyst such as p-toluenesulfonic acid or benzenesulfonic acid. The two compounds are preferably mixed in equimolar quantities. The acid catalyst is used in an amount of 0.01 to 10% by mole based on the moles of the dioxane or dioxepane, preferably 0.1 to 5% by mole on the same basis.

The reaction is conducted at a temperature in a range of $-78°$ to $100°$ C., preferably $-20°$ to $50°$ C. and generally under an atmosphere of an inert gas such as nitrogen, argon or helium.

The reaction may be conducted in the absence of any solvent but, preferably, in the presence of a solvent such as a halohydrocarbon, e.g. methylene chloride, chloroform and tetrachloroethylene because of ready removal of reaction heat and ready operability.

The reaction time is generally selected from a range from 1 to 100 hours. After the desired conversion ratio has been attained, the reaction mixture is washed with an aqueous alkaline solution such as sodium hydroxide o potassium hydroxide and, then, the spiroorthocarbonate represented by the formula (11) is isolated and purified in the usual manner.

Yet another species of the spiroorthocarbonate compound of the present invention are those of the formula (1) with A

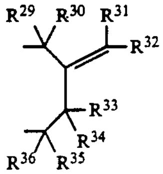

(16)

, i.e.

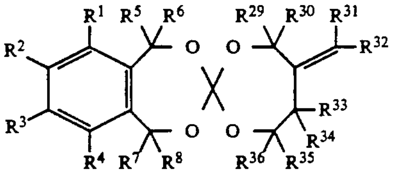

wherein $R^1$ through $R^8$ are as defined before, and $R^{29}$ through $R^{36}$ each represents a hydrogen atom or a lower alkyl group having not more than 8 carbon atoms. Concrete examples of the lower alkyl group having not more than 8 carbon atoms are as given before.

Concrete examples of the compound are as follows.

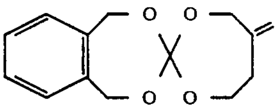

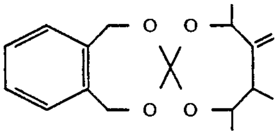

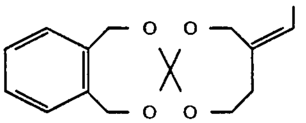

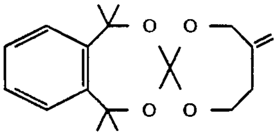

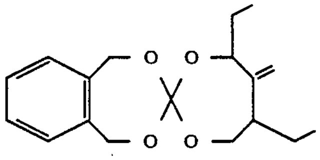

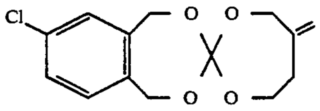

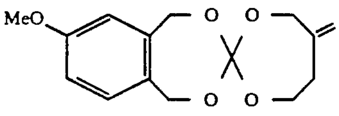

-continued

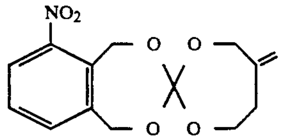

The spiroorthocarbonate compound represented by the formula (16) may be produced in the same manner as described for that represented by the formula (11) except for using, instead of a diol represented by the formula (13), one represented by the following formula (17)

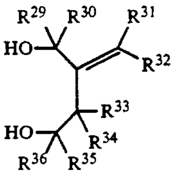

(17)

wherein $R^{29}$ through $R^{36}$ are as defined above.

The spiroorthocarbonate compounds of the present invention undergo ring-opening isomerization polymerization in the presence of a cationic polymerization initiator such as boron trifluorideether complex, or an azobis-based polymerization initiator such as azobisisobutyronitrile or azobiscyclohexanecarbonitrile, or a peroxide-based polymerization initiator such as diisopropyloxy dicarbonate, 2,4-dichlorobenzoyl peroxide, lauroyl peroxide, benzoyl peroxide, cyclohexanone peroxide, t-butyl perbenzoate, dicumyl peroxide, di-t-butyl peroxide, p-menthane hydroperoxide, pinane hydroperoxide, cumene hydroperoxide or t-butyl hydroperoxide. There may also be employed ultraviolet radical polymerization utilizing an initiator, e.g. aromatic ketones such as benzophenone, Michler's ketone, xanthone, thioxanthone, 2chlorothioxanthone and 2-ethylanthraquinone and acetophenones such as acetophenone, trichloroacetophenone, 2-hydroxy-2-methylpropiophenone, 2-hydroxy- 2-methyl-4'-isopropylpropiophenone, 1-hydroxycyclohexyl phenyl ketone, benzoin isopropyl ether, benzoin isobutyl ether, 2,2-diethoxyacetophenone and 2,2-dimethoxy-2-phenylacetophenone benzyldimethyl ketal; and visible light radical polymerization utilizing an α-diketone/amine-based initiator such as camphorquinone/N,N-dimethylaminoathyl methacrylate, norcamphorquinone/N,N-dimethylaminoethyl methacrylate or camphorquinone/ethyl p-N,N-dimethylaminobenzoate.

The above polymerization initiator is used in an amount of 0.01 to 10% by mole based on the moles of the spiroorthocarbonate compound, preferably 0.05 to 3% by mole on the same basis.

The polymerization reaction is conducted at a temperature, although depending on the type of the initiator used, of room temperature to 200° C., preferably 50° to 180° C.

The polymerization reaction may be conducted under any pressure ranging from reduced pressure to elevated pressure, but preferably conducted under atmospheric pressure.

The polymerization reaction may be conducted in the absence of solvent but, preferably, conducted in the presence of an aromatic hydrocarbon such as benzene, toluene, xylene, hemimellitene, pseudocumene or mesitylene; an aliphatic hydrocarbon such-as hexane, heptane or octane; an alicyclic hydrocarbon such as cyclohexane or cyclooctane; or a halohydrocarbon such as methylene chloride, chloroform, tetrachloroethylene, chlorobenzene, dichlorobenzene or trichlorobenzene.

The polymerization reaction time is generally selected from a range from 1 to 100 hours. After the desired degree of polymerization has been attained, the obtained polymer is isolated and purified in the usual manner.

In the present invention, the polymer obtained by polymerization of the spiroorthocarbonate consists of a moiety formed by vinyl polymerization and a moiety formed by ring-opened isomerization polymerization. A polymer exhibits decrease in shrinkage or expansion in volume on polymerization with increase in the moiety formed by the ring-opened isomerization polymerization in the polymer. According to the present invention, the polymer may contain the moiety formed by ring-opened isomerization polymerization by 5 to 95 mol %.

The moiety formed by the ring-opened polymerization from the spiroorthocarbonate compound (2) or (9) has a structure of polyketone carbonate in which the spiro rings have undergone double ring opening, and that from the spiroorthocarbonate compound (11) or (16) has a structure of polyether carbonate with the spiro rings opened in the same manner.

The spiroorthocarbonate compounds of the present invention may be polymerized alone or in admixtures of 2 or more. Further the spiroorthocarbonate compounds of the present invention may be polymerized in combination with other ethylenic monomer. Any ethylenic monomer that can undergo radical polymerization may be used for this purpose and its examples are (meth)acrylic acid, (meth)acrylates, acrylonitrile, acrylamide, vinyl chloride, vinyl acetate and styrene. Preferred examples of usable (meth)acrylates are monofunctional and multifunctional (meth)acrylates, such as alkyl (meth)acrylates having 1 to 10 carbon atoms in the alkyl group, polyalkylene glycol di(meth)acrylates having 2 to 20 carbon atoms in the alkylene group, ethylene glycol oligomer di(meth)acrylates containing 2 to 10 monomeric units, bisphenol A di(meth)acrylate, 2,2-bis[p-(γ-methacryloxy-β-hydroxypropoxy)phenyl]propane, 2,2-di(4-methacryloxypolyeth-oxyphenyl)propane having 2 to 10 ethoxy groups per molecule, trimethylolpropane tri(meth)acrylate and pentaerythritol tetra(meth)acrylate; and urethane (meth)acrylates obtained by reacting a (meth)acrylate having hydroxyl group and a diisocyanate in a molar ratio of 2/1, or, more concretely, those obtained by reacting both molecular ends of a monomer as disclosed in Japanese patent publication No. 33687/1980 or Japanese patent Application Laid-open No. 152408/1981 or bisphenol A modified With ethylene glycol, with 2 molecules of a diisocyanate and then bonding one molecule each of a (meth)acrylate having hydroxyl group to both ends of the obtained product.

Where a spiroorthocarbonate compound of the present invention does not yield sufficiently ring-opened polymers, the compound may be copolymerized with a compound (hereinafter referred to as "benzylsulfonium ethylene") having the following benzylsulfonium salt structure (18)

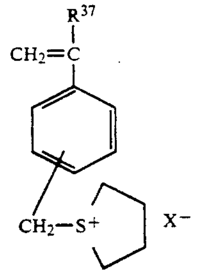

(18)

wherein $R^{37}$ represents a hydrogen atom or a lower alkyl group having not more than 8 carbon atoms and $X^-$ represents an anion selected from $SbF_6^-$, $AsF_6^-$, $pF_6^-$ or $BF_4^-$, and, if necessary, with other ethylenic monomer to yield a copolymer, which can then be heated to yield a crosslinked polymer that shows expansion upon curing.

The sulfonium salt of the benzylsulfonium ethylene acts as catalyst for ring-opened isomerization polymerization of the spiroorthocarbonate moiety by heating, whereby the crosslinked polymer is obtained.

Heating of the polymer at high temperature causes ring-opened isomerization to occur to a large extent. In the present invention, the polymer is generally heated at a temperature of 80° to 300° C., more preferably 100° to 150° C.

The copolymer obtained consists of the following repeating units L, M and N

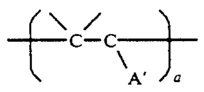

(L)

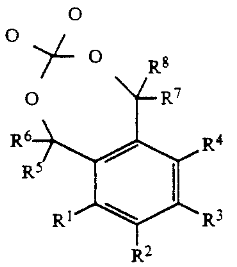

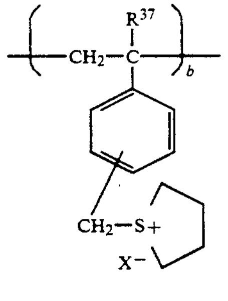

(M)

$$-\!\!(E)\!\!-_c$$

(N)

wherein 1≦a≦99.9, 0.1≦b≦30 and 0≦c≦99, and A' in L represents the residue obtained by removing exomethylene group from A in the general formula (1) and E in N represents the other ethylenic monomer.

Units from benzylsulfonium ethylene are contained in the polymer in an amount of 0.1 to 30 mol %, preferably 3 to 20 mol %. With the content being less than 0.1 mol %, sufficient curing is not achieved; while With the content exceeding 30 mol % there occur discoloration of cured material.

The spiroothocarbonate compounds of the present invention are used for various purposes, as polymerizable compositions that give polymerization-expanding polymers. The compositions contain one or more of the spiroorthocarbonate, comonomer and polymerization initiator. The compositions may, depending on the type of the polymerization initiator used, be packed in 2 packs, or packed separately from the initiator. Concrete examples of the application of the compositions include molding compositions, adhesives and dental compositions.

For dental compositions, which require high hardness, strength and abrasion resistance after curing, the spiroorthocarbonate compounds of the present invention can be used with fillers added thereto.

Examples of the fillers for this purpose are quartz powder, alumina powder, hydroxyapatite, calcium carbonate, fluoroaluminosilicate glass, barium sulfate, titanium dioxide, zirconia powder, glass powder, ultrafine particulate silica and organic composite fillers containing both organic and inorganic components. Examples of the glass among the above are silica glass, soda lime silicate glass, borosilicate glass, barium boroaluminosilicate glass, aluminasilicate glass, strontium boroaluminosilicate glass, synthetic silica and titanium silicate glass. powder of polymers such as polymethyl methacrylate, polystyrene and polyvinyl chloride may as required be also incorporated.

It is desirable that inorganic fillers used for the above purpose be surface-treated. Usable for this purpose are organosilicon compounds, e.g. γ-methacryloxypropyltrimethoxysilane, vinyltrichlorosilane, vinyltriethoxysilane, vinyltrimethoxysilane, vinyltriacetoxysilane and vinyltri(methoxyethoxy)silane. The silane-treatment may be conducted in the usual manner.

Other features of the invention will become apparent in the course of the following descriptions of exemplary embodiments which are given for illustration of the invention and are not intended to be limiting thereof.

EXAMPLES

Example 1

The air inside a 100-ml glass vessel equipped with a stirrer was fully replaced by dry nitrogen gas. The vessel was then charged with 9.48 g (76 mmoles) of 4-chloro-1,3-butanediol, 15.4 g (152 mmoles) of triethylamine and 40 ml of methylene chloride. To the mixture, a solution of 20.5 g (76 mmoles) of diphenoxydichloromethane in 50 ml of methylene chloride was added with stirring at a temperature of 25° C. over 80 minutes. After being stirred at a room temperature for S hours, the mixture was washed three times With 40 ml of water and the organic layer was separated from water layer. The organic layer was dried over anhydrous sodium sulfate, concentrated and then distilled under reduced Pressure, to give 11.1 g of a colorless transparent liquid boiling at 182° C./0.35 mmHg. The liquid thus obtained was identified by $^1$H-NMR spectrometry and IR spectrometry to be 2,2-diphenoxy-4-chloromethyl-1,3-dioxane. The Yield was 45%.

$^1$H-NMR—the spectrum is shown in FIG. 1.
Solvent: deuterated chloroform
Internal standard reference: tetramethylsilane

TABLE 1

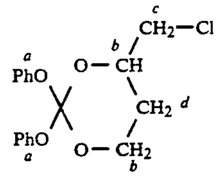

| | δ (ppm) | Peak area ratio | Multiplicity |
|---|---|---|---|
| d | 1.50 to 2.30 | 2H | multiplet |
| c | 3.48 | 2H | doublet |
| b | 3.60 to 4.48 | 3H | multiplet |
| a | 7.00 to 7.22 | 10H | multiplet |

Figure 2:
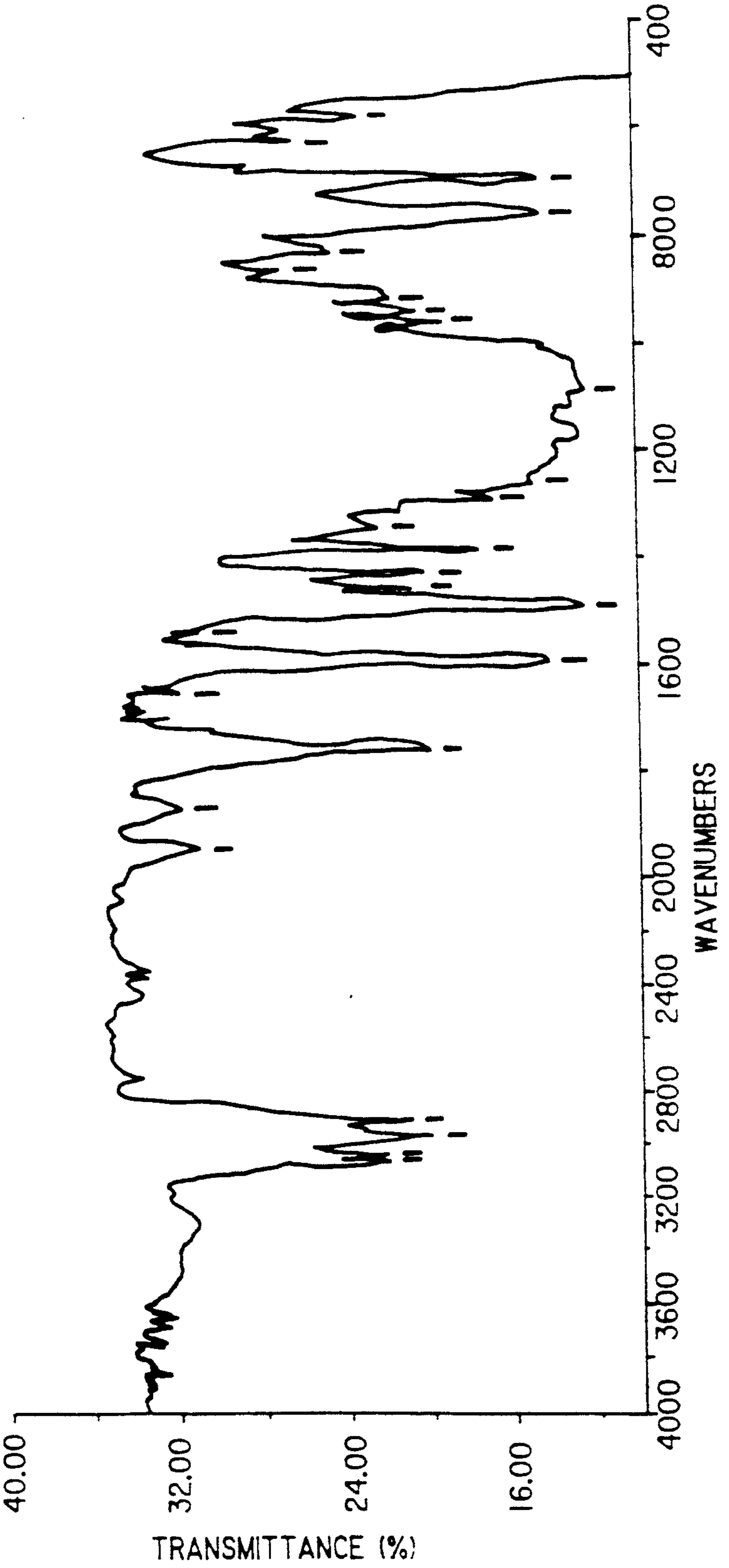
FIGS. 2 and 4 show IR spectra of the above dioxane and spirodioxane, respectively.

The IR spectrum is shown in FIG. 2.

The air inside a 100-ml glass vessel equipped with a stirrer was fully replaced by dry nitrogen gas. The vessel was then charged with 11.1 g (35 mmoles) of the 2,2-diphenoxy-4-chloromethyl-1,3-dioxane obtained in the above reaction, 196 mg (1.04 mmoles) of p-toluenesulfonic acid monohydrate and 40 ml of methylene chloride. To the mixture, 4.76 g (35 mmoles) of o-xylylene glycol was added with stirring at a temperature of 25° C. Stirring was continued at 25° C. for 50 hours, and then 40 ml of 2N sodium hydroxide solution was added. The organic layer was separated from water layer and washed twice with 80 ml of 2N sodium hydroxide solution. The organic layer was dried over anhydrous sodium sulfate, and then concentrated, whereby white solid precipitated. The white solid was purified by recrystallization from a 3/1 by volume mixed solvent of n-hexane/ethyl acetate, to give 8.70 g of colorless crystal. The crystal thus obtained was identified by $^1$H-NMR spectrometry and IR spectrometry to be spiro[1,5-dihydro-2,4-benzodioxepin-4'-chloromethyl-3,2'-[1,3]dioxane]. The yield was 93%.

Figure 3:
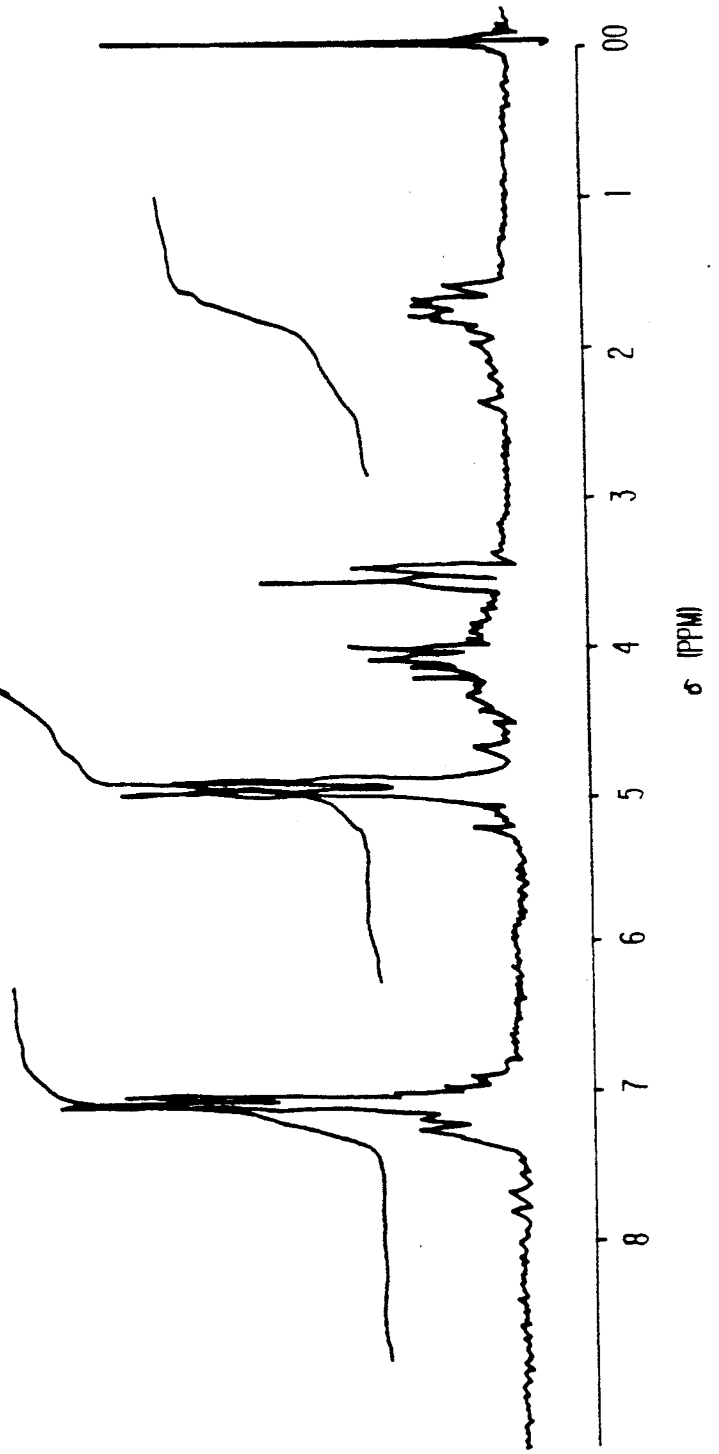

$^1$H-NMR—the spectrum is shown in FIG. 3.
Solvent: deuterated chloroform
Internal standard reference: tetramethylsilane

TABLE 2

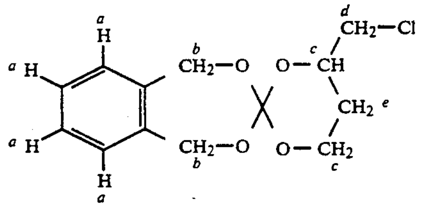

| | δ (ppm) | Peak area ratio | Multiplicity |
|---|---|---|---|
| e | 1.60 to 2.00 | 2H | multiplet |
| d | 3.55 | 2H | doublet |
| c | 3.83 to 4.45 | 3H | multiplet |
| b | 4.89 | 2H | singlet |
| b | 5.00 | 2H | singlet |
| a | 6.90 to 7.25 | 4H | multiplet |

Figure 4:
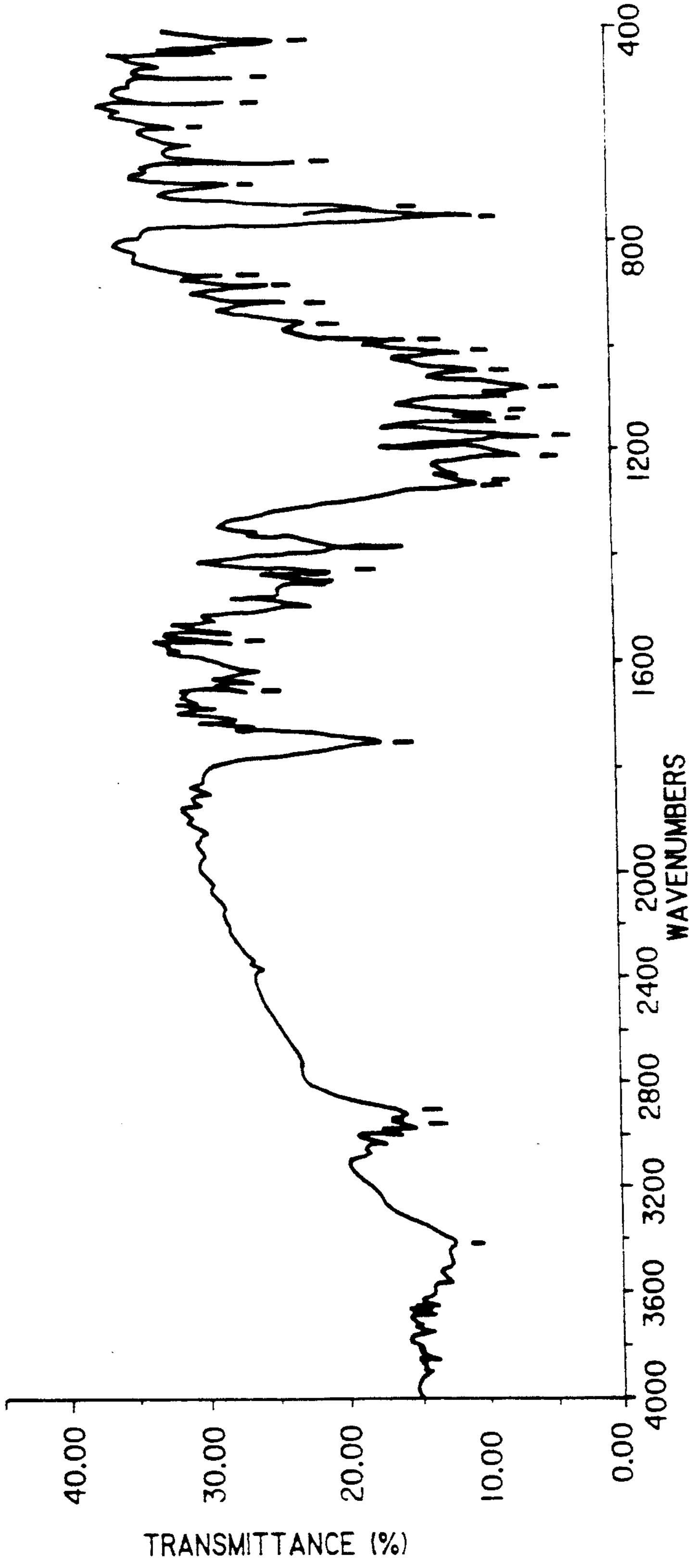

The IR spectrum is shown in FIG. 4.

The air inside a 50-ml glass vessel equipped with a stirrer was fully replaced by dry nitrogen gas. The vessel was then charged with 2.19 g (41 mmoles) of sodium methoxide and 30 ml of dimethylformamide. To the mixture was added a solution of 8.46 g (31 mmoles) of the spiro[1,5-dihydro-2,4-benzodioxepin-4'-chloromethyl-3,2'-[1,3]dioxane] obtained in the above reaction in 18 ml of dimethylformamide with stirring at a temperature of 25° C. over 30 minutes. Stirring was continued at 25° C. for 100 hours, and then 180 ml of water was added. Organic matter in the water layer was extracted with 90 ml of ether. The extracted layer was dried over anhydrous sodium sulfate, and then concentrated, whereby white solid precipitated. The white solid was purified by recrystallization from 12 ml of a 3/1 by volume mixed solvent of n-hexane/ethyl acetate, to give 4.08 g of colorless crystal. The crystal thus obtained was identified by $^1$H-NMR spectrometry and IR spectrometry to be spiro[1,5-dihydro-2,4-benzodioxepin-4'-methylene-3,2'-[1,3]dioxane]. The yield was 74%.

Figure 5:
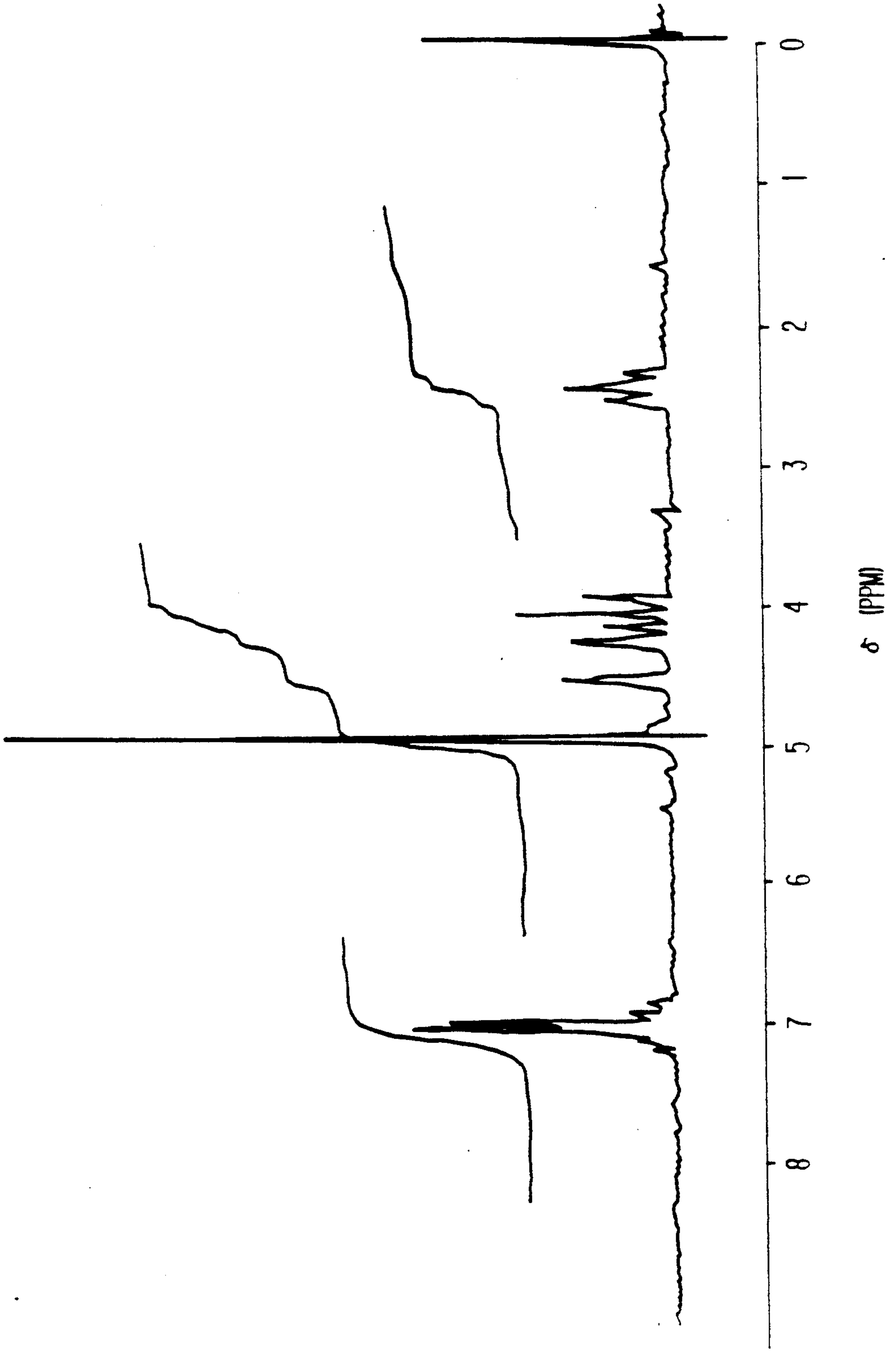
FIGS. 5 and 6 show an $^1$H-NMR spectrum and an IR spectrum of the spiroorthocarbonate obtained in Example 1, respectively.

$^1$H-NMR—the spectrum is shown in FIG. 5.
Solvent: deuterated chloroform
Internal standard reference: tetramethylsilane

TABLE 3

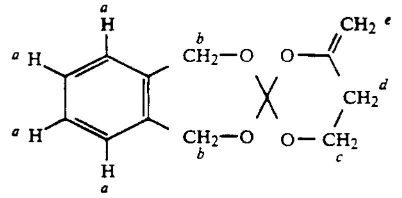

| | δ (ppm) | Peak area ratio | Multiplicity |
|---|---|---|---|
| d | 2.43 | 2H | triplet |
| c | 4.03 | 2H | triplet |
| e | 4.23 | 1H | singlet |
| e | 4.52 | 1H | singlet |
| b | 4.95 | 4H | singlet |
| a | 6.82 to 7.19 | 4H | multiplet |

Figure 6:
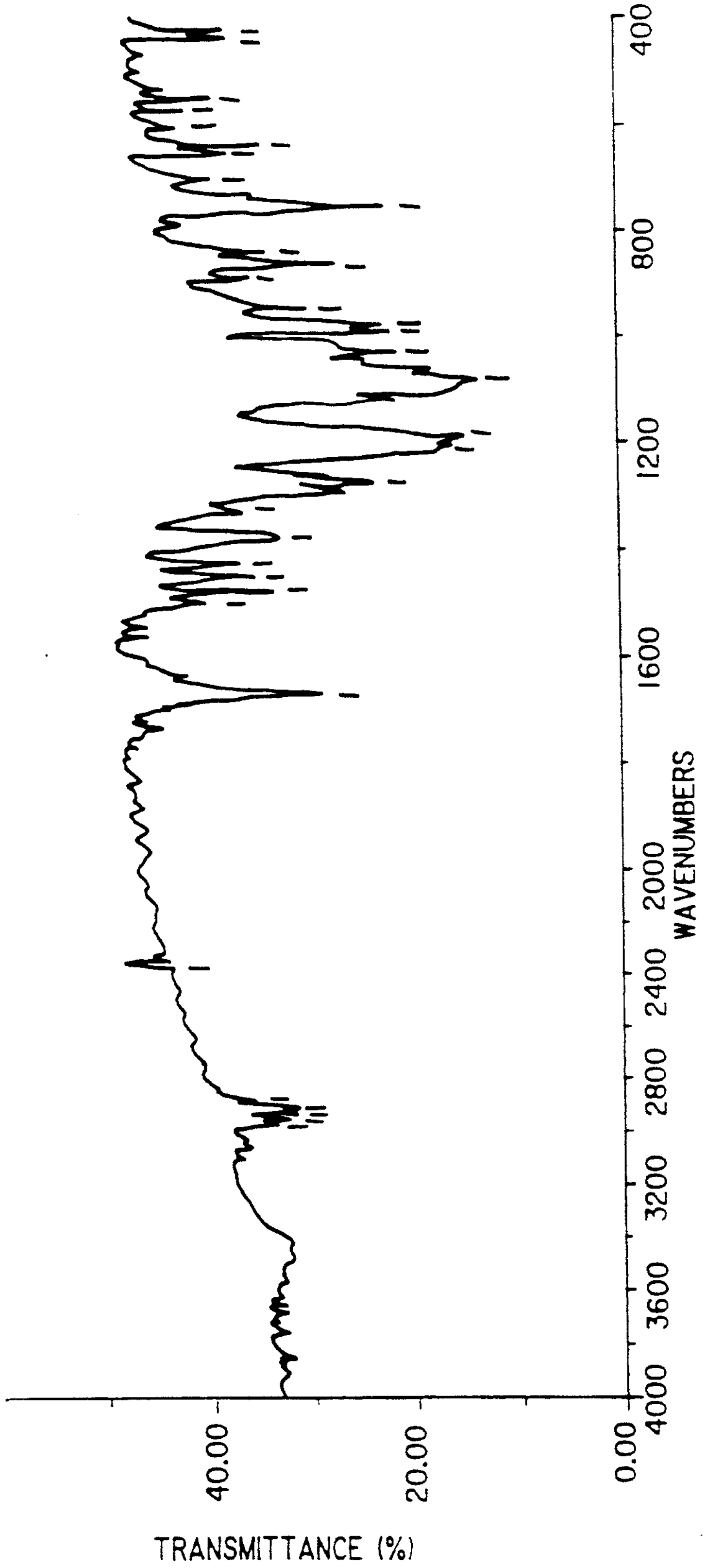

The IR spectrum is shown in FIG. 6.

TABLE 4

| | Elemental analysis | |
|---|---|---|
| | C % | H % |
| Observed | 66.58 | 6.31 |
| Calculated as $C_{13}H_{14}O_4$ | 66.66 | 6.02 |

Melting Point: 73° to 74° C.
Density: 1.310

Example 2

Example 1 was repeated except for using 6.00 g (35 mmoles) of 4-chloro-o-xylylene glycol, instead of 4.76 g (35 mmoles) of o-xylylene glycol, to obtain spiro[7-chloro-1,5-dihydro-2,4-benzodioxepin-4'-methylene-3,2'-[1,3]dioxane].

TABLE 5

| | Elemental analysis | |
|---|---|---|
| | C % | H % |
| Observed | 57.98 | 4.97 |
| Calculated as $C_{13}H_{14}O_4Cl$ | 58.11 | 4.88 |

Example 3

Example 1 was repeated except for using 10.53 g (76 mmoles) of 2-methyl-4-chloro-1,3-butanediol and 6.00 g (35 mmoles) of 4-chloro-o-xylylene glycol, instead of 9.48 g (76 mmoles of 4-chloro-1,3-butanediol and 4.76 g (35 mmoles) of o-xylylene glycol, respectively, to obtain spiro[7-chloro-1,5-dihydro-2,4-benzodioxepin-4'-methylene-5'-methyl-3,2'-[1,3dioxane.

TABLE 6

| | Elemental analysis | |
|---|---|---|
| | C % | H % |
| Observed | 59.22 | 5.17 |
| Calculated as $C_{14}H_{15}O_4Cl$ | 59.48 | 5.35 |

Example 4

A glass vessel was charged with 234 mg of the spiro[1,5-dihydro-2,4-benzodioxepin-4'-methylene-3,2'-[1,3]-dioxane] obtained in Example 1 and 2.7 mg of t-butyl hydroperoxide. The contents were degassed and the vessel was sealed. The vessel and the contents were heated at 180° C. for 4 hours, to give a pale yellow transparent solid. The solid thus obtained was dissolved in 2 ml of methylene chloride and reprecipitated from 50 ml of n-hexane, to give 89 mg of a transparent liquid. The Product obtained had a number average molecular weight of 1,160 and a molecular weight distribution of 2.68.

The product was measured for IR spectrum, which showed an absorption at 1,753 $cm^{-1}$ originating from the carbonate of a ring-opened polymer and one at 1,720 $cm^{-1}$ originating from the ketone of the ring-opened polymer.

The product had a density of 1.228 g/$cm^3$, from which the expansion in volume is calculated, based on the monomer density, to be 6.3%.

Example 5

Example 4 was repeated except for using, instead of 234 mg of the spiro[1,5-dihydro-2,4-benzodioxepin-4'-methylene-3,2'-[1,3]dioxane], 268 mg of the spiro[7-chloro-1,5-dihydro- 2,4-benzodioxepin-4'-methylene-3,2'-[1,3dioxane] obtained Example 2, to conduct polymerization and obtain a polymer having a number average molecular weight of 1,370 and a molecular weight distribution of 2.33. The expansion in volume based on-the monomer density was 5.7%.

Example 6

Example 4 was repeated except for using, instead of 234 mg of the spiro[1,5-dihydro-2,4-benzodioxepin-4'-methylene-3,2'-[1,3]dioxane], 282 mg of the spiro[7-chloro-1,5-dihydro-2,4-benzodioxepin-4'-methylene-5'-methyl-3,2'-[1,3]dioxane] obtained in Example 3, to conduct polymerization and obtain a polymer having a number average molecular weight of 1,540 and a molecular weight distribution of 2.21. The expansion in volume based on the monomer density was 6.5%.

Example 7

Example 4 was repeated except for using, instead of 234 mg of the spiro[1,5-dihydro-2,4-benzodioxepin-4'-methylene-3,2'-[1,3]dioxane], a mixture of 117 mg of spiro[1,5-dihydro-2,4-benzodioxepin-4'-methylene-3,2'-[1,3]dioxane] and 50 mg of methyl methacrylate, to conduct polymerization and obtain a polymer having a number average molecular weight of 2,970 and a molecular weight distribution of 2.09. The expansion in volume based on the monomer density was −0.5%.

Example 8

The air inside a 100-ml glass vessel equipped with a stirrer was fully replaced by dry nitrogen gas. The vessel was then charged with 19.0 g (137 mmoles) of 5-chloro-1,4-pentanediol, 27.8 g (274 mmoles) of triethylamine and 70 ml of methylene chloride. To the mixture, a solution of 36.9 g (137 mmoles) of diphenoxydichloromethane in 80 ml of methylene chloride was added with stirring at a temperature of 25° C. over 30 minutes. After being stirred at a room temperature for 8 hours, the mixture was washed three times with 200 ml of 1N sodium hydroxide solution and the organic layer was separated from water layer. The organic layer was dried over anhydrous sodium sulfate, concentrated and then distilled under reduced pressure, to give 22.9 g of a colorless transparent liquid boiling at 178° C./0.6 mmHg. The liquid thus obtained was identified by $^1$H-NMR spectrometry and IR spectrometry to be 2,2-diphenoxy-4-chloromethyl-1,3-dioxepane. The yield was 50%.

Figure 7:
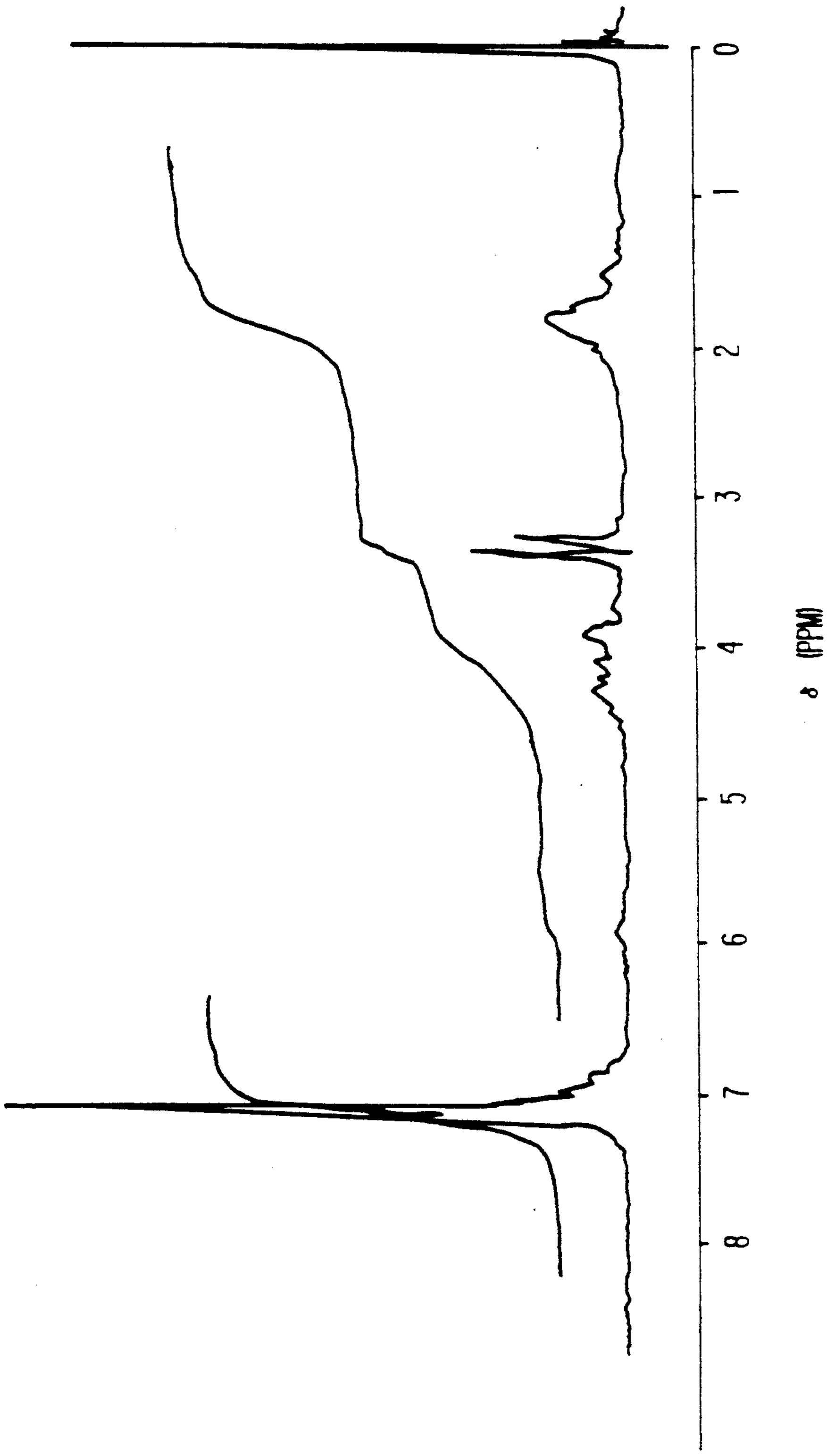
FIGS. 7 and 9 show $^1$H-NMR spectra of the dioxepane and spirodioxepane produced as intermediates in Example 8, respectively.

$^1$H-NMR—the spectrum is shown in FIG. 7.

Solvent: deuterated chloroform

Internal standard reference: tetramethylsilane

TABLE 7

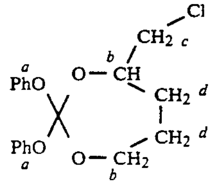

| | δ (ppm) | Peak area ratio | Multiplicity |
|---|---|---|---|
| d | 1.35 to 2.20 | 4H | multiplet |
| c | 3.31 | 2H | doublet |
| b | 3.83 to 4.48 | 3H | multiplet |
| a | 6.83 to 7.30 | 10H | multiplet |

Figure 8:
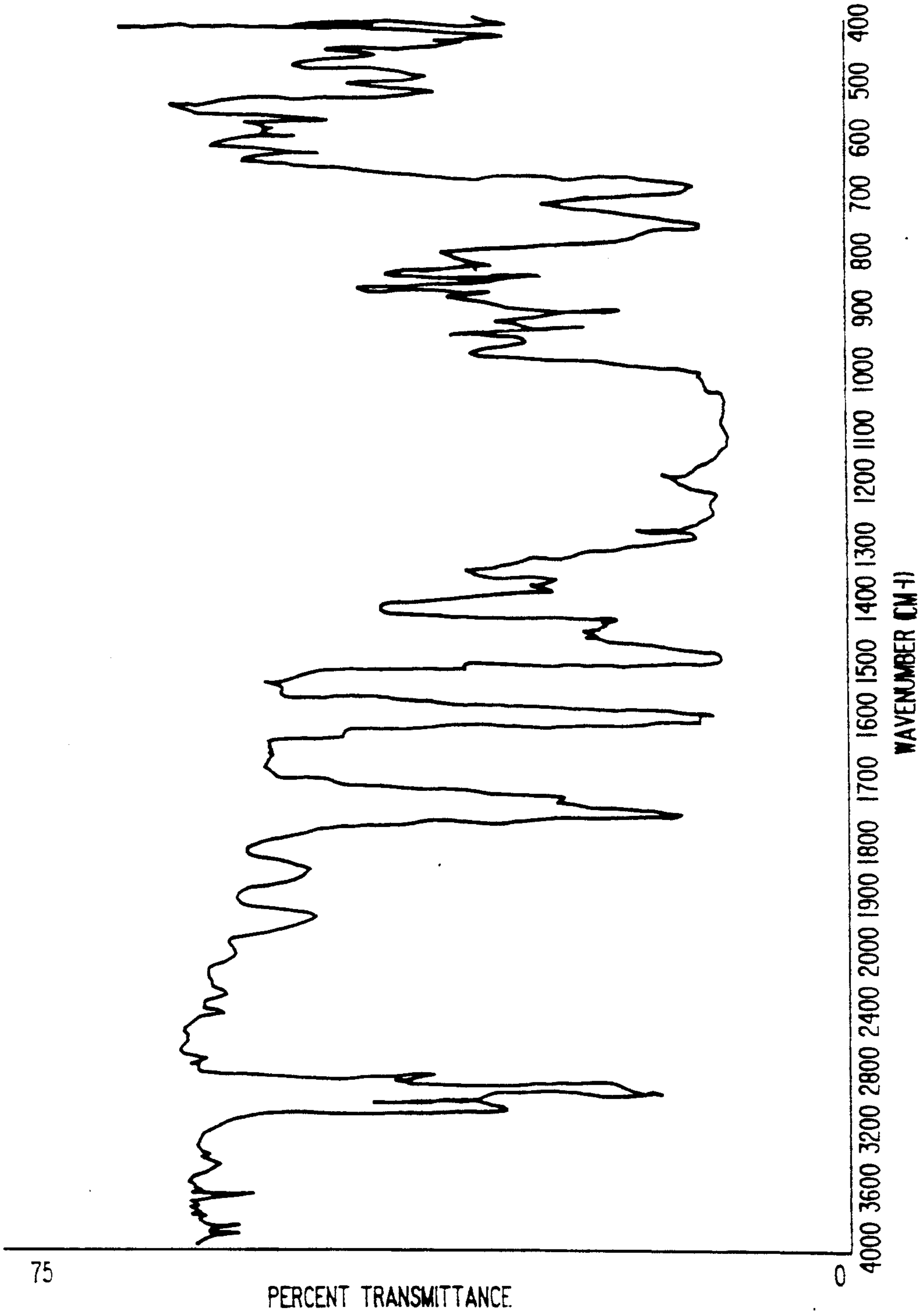
FIGS. 8 and 10 show IR spectra of the above dioxepane and spirodioxepane, respectively.

The IR spectrum is shown in FIG. 8.

The air inside a 100-ml glass vessel equipped with a stirrer was fully replaced by dry nitrogen gas. The vessel was then charged with 9.58 g (28.6 mmoles) of the 2,2-diphenoxy-4-chloromethyl-1,3-dioxepane obtained in the above reaction, 272 mg (1.43 mmoles) of p-toluenesulfonic acid monohydrate and 50 ml of methylene chloride. To the mixture, 3.95 g (28.6 mmoles) of o-xylylene glycol was added with stirring at a temperature of 25° C. Stirring was continued at 25° C. for 48 hours, and then 50 ml of 2N sodium hydroxide solution was added. The organic layer was separated from water layer and washed twice with 100 ml of 2N sodium hydroxide solution. The organic layer was dried over anhydrous sodium sulfate, and then concentrated, whereby white solid precipitated. The white solid was purified by recrystallization from a 3/1 by volume mixed solvent of n-hexane/ethyl acetate, to give 4.35 g of colorless crystal. The crystal thus obtained was identified by $^1$H-NMR spectrometry and IR spectrometry to be spiro[1,5-dihydro-2,4-benzodioxepin-4'-chloromethyl-3,2'-[1,3]dioxepane]. The yield was 53%.

Figure 9:
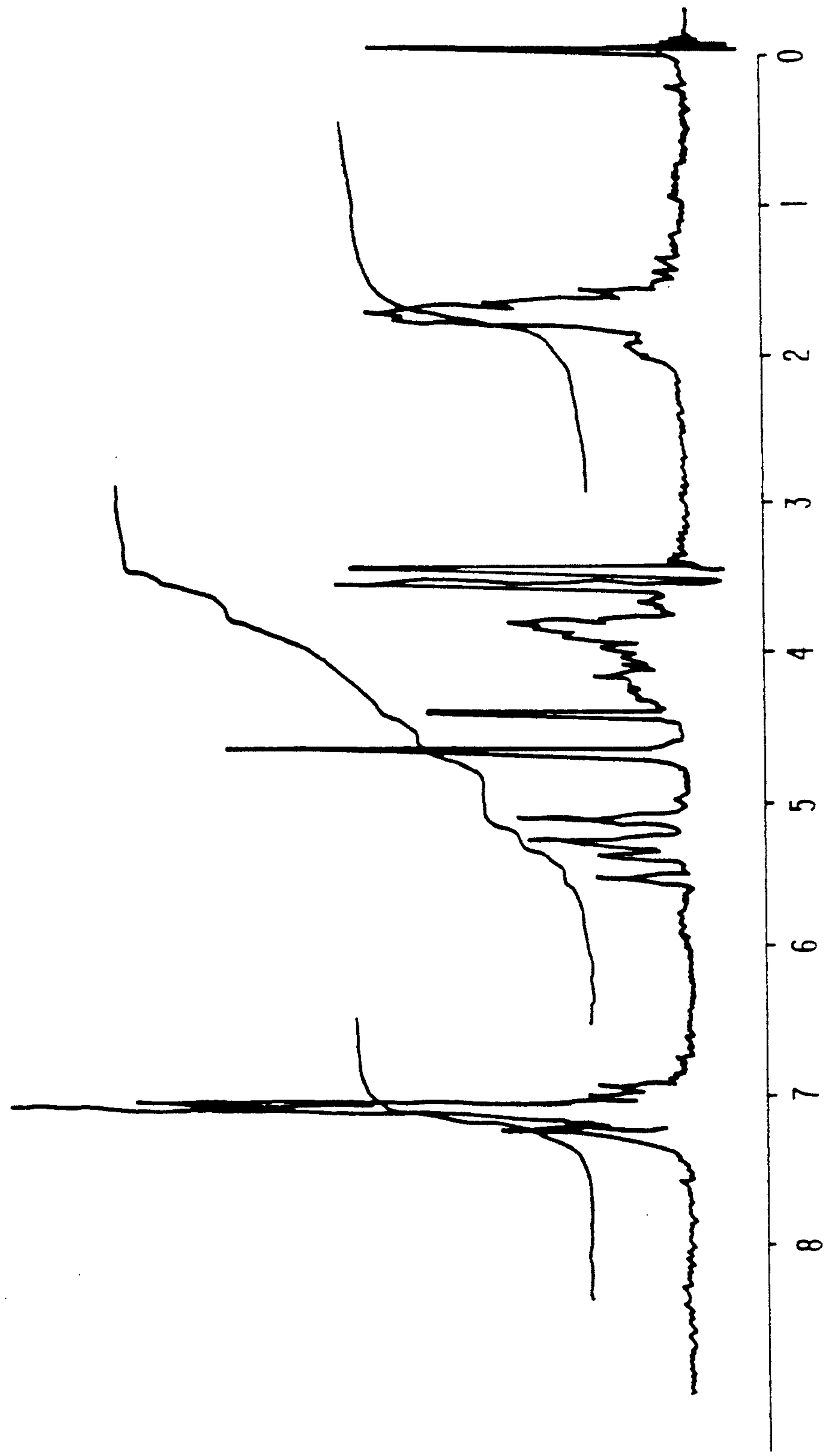

$^1$H-NMR—the spectrum is shown in FIG. 9.

Solvent: deuterated chloroform

Internal standard reference: tetramethylsilane

TABLE 8

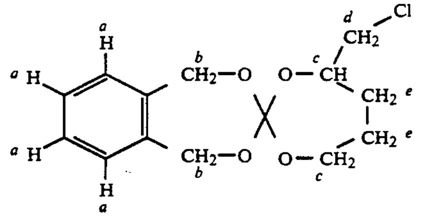

| | δ (ppm) | Peak area ratio | Multiplicity |
|---|---|---|---|
| e | 1.33 to 2.05 | 4H | multiplet |
| d | 3.52 | 2H | doublet |
| c | 3.60 to 4.39 | 3H | multiplet |
| b | 4.40 to 5.53 | 4H | multiplet |
| a | 6.89 to 7.23 | 4H | multiplet |

Figure 10:
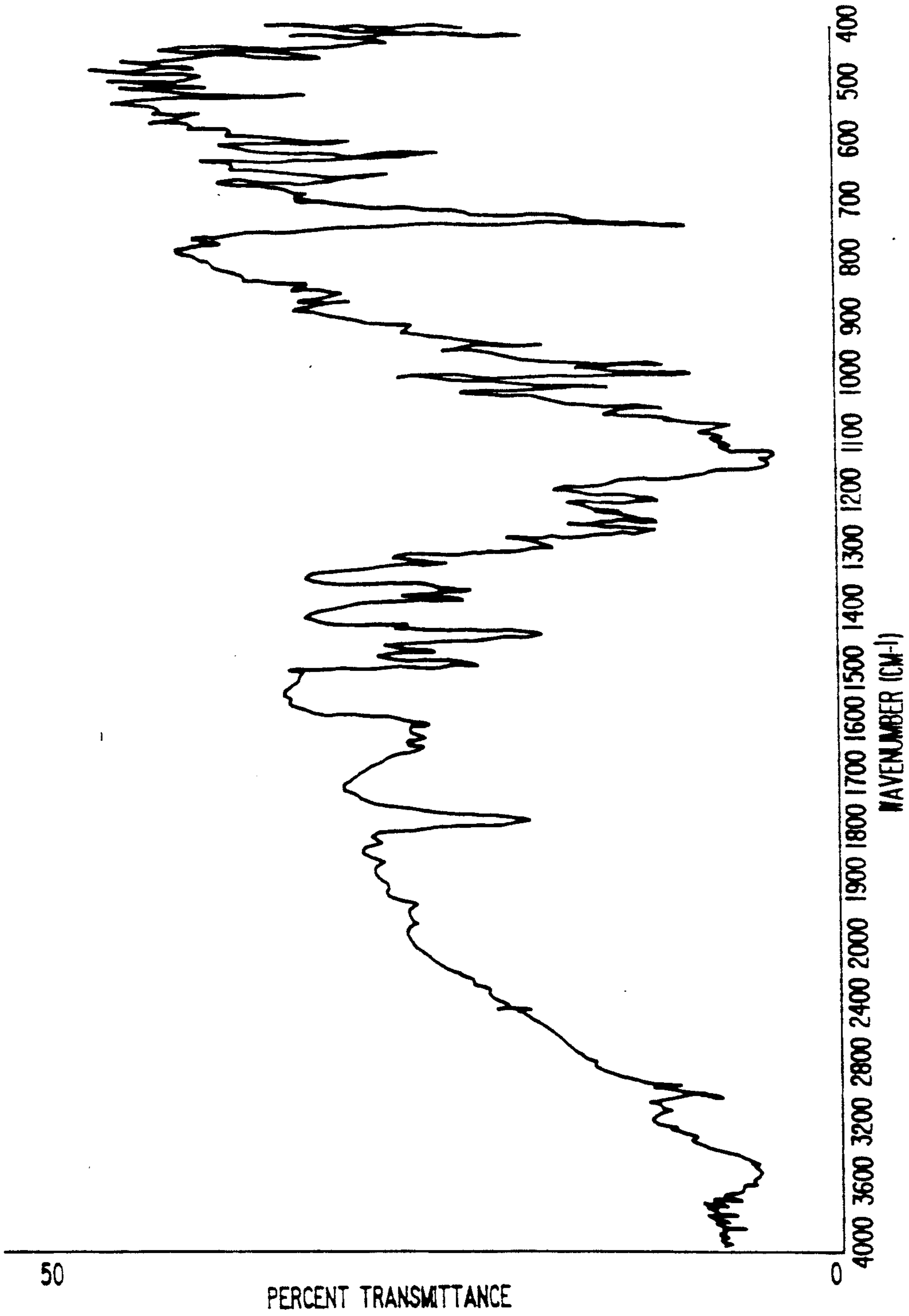

The IR spectrum is shown in FIG. 10.

The air inside a 100-ml glass vessel equipped with a stirrer was fully replaced by dry nitrogen gas. The vessel was then charged With 1.51 g (28 mmoles) of sodium methoxide and 30 ml of dimethylformamide. To the mixture was added a solution of 4.0 g (14 mmoles) of the spiro[1,5-dihydro-2,4-benzodioxepin-4'-chloromethyl-3,2'-[1,3]dioxepane] obtained in the above reaction in 20 ml of dimethylformamide with stirring at a temperature of 25° C. over 30 minutes. Stirring was continued at 25° C. for 10 hours, and then 50 ml of water was added. Organic matter in the water layer was extracted with 50 ml of ether. The extracted layer was dried over anhydrous sodium sulfate, and then concentrated, whereby white solid precipitated. The white solid was purified by recrystallization from a 3/1 by volume mixed solvent of n-hexane/ethyl acetate, to give 2.99 g of colorless crystal. The crystal thus obtained was identified by $^1$H-NMR spectrometry and IR spectrometry to be spiro[2,4-benzodioxepin-4'-methylene-3,2'-[1,3]dioxepane]. The yield was 86%.

Figure 11:
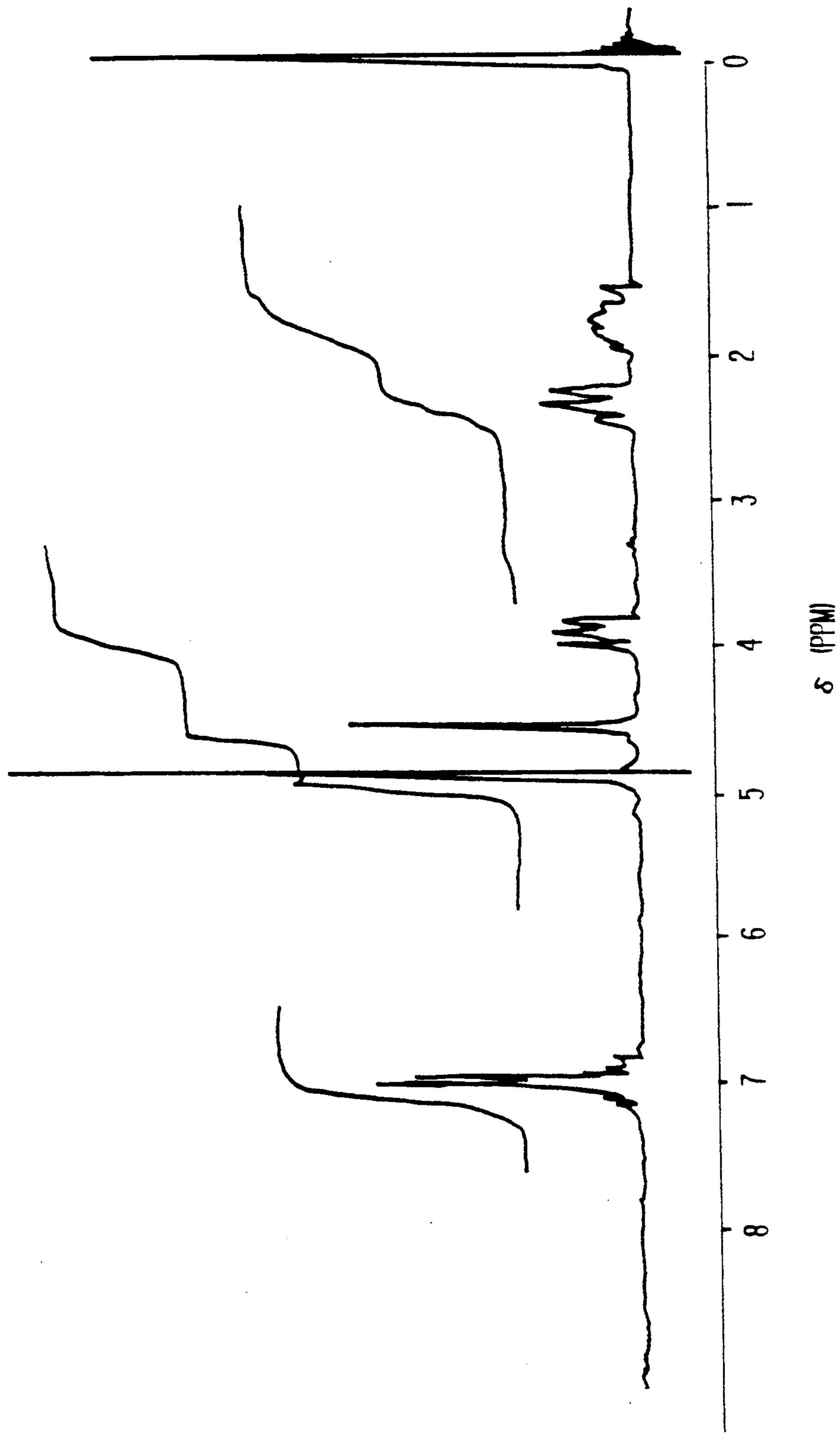
FIGS. 11 and 12 show an $^1$H-NMR spectrum and an IR spectrum of the spiroorthocarbonate obtained in Example 8.

$^1$H-NMR—the spectrum is shown in FIG. 11.

Solvent: deuterated chloroform

Internal standard reference: tetramethylsilane

TABLE 9

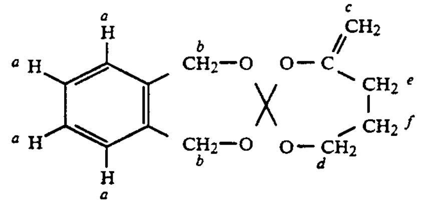

| | δ (ppm) | Peak area ratio | Multiplicity |
|---|---|---|---|
| f | 1.58 to 1.97 | 2H | multiplet |
| e | 2.36 | 2H | triplet |
| d | 3.93 | 2H | triplet |
| c | 4.57 | 2H | singlet |
| b | 4.90 | 4H | singlet |
| a | 6.79 to 7.15 | 4H | multiplet |

Figure 12:
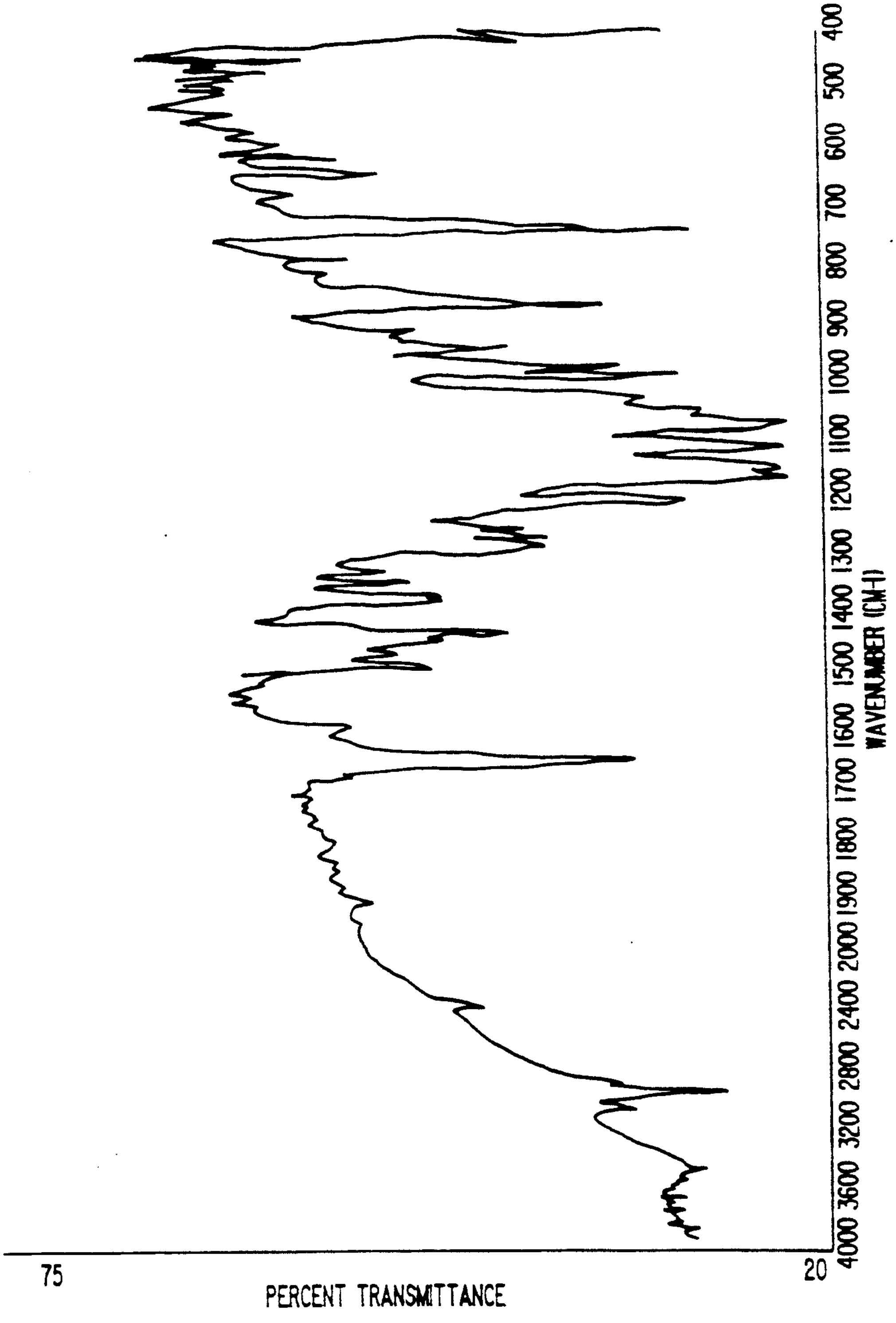

The IR spectrum is shown in FIG. 12.

TABLE 10

| | Elemental analysis | |
|---|---|---|
| | C % | H % |
| Observed | 67.57 | 6.44 |
| Calculated as $C_{14}H_{16}O_4$ | 67.73 | 6.50 |

Melting point: 88° to 90° C.

Density: 1.340

Example 9

Example 8 was repeated except for using 4.94 g (28.6 mmoles) of 4-chloro-o-xylylene glycol, instead of 3.95 g (28.6 mmoles) of o-xylylene glycol, to obtain spiro[7-chloro- 1,5-dihydro-2,4-benzodioxepin-4'-methylene-3,2'-[1,3]dioxepane].

TABLE 11

| | Elemental analysis C % | H % |
|---|---|---|
| Observed | 59.32 | 5.55 |
| Calculated as $C_{14}H_{15}O_4Cl$ | 59.48 | 5.35 |

Example 10

Example 8 was repeated except for using 20.9 g (137 mmoles) of 3-methyl-5-chloro-1,4-pentanediol and 4.94 g (28.6 mmoles) of 4-chloro-o-xylylene glycol, instead of 19.0 g (137 mmoles) of 5-chloro-1,4-pentanediol and 3.95 g (28.6 mmoles) of o-xylylene glycol, respectively, to obtain spiro[7-chloro-1,5-dihydro-2,4-benzodioxepin-4'-methylene-5'-methyl-3,2'-[1,3]dioxepane].

TABLE 12

| | Elemental analysis C % | H % |
|---|---|---|
| Observed | 61.00 | 5.57 |
| Calculated as $C_{15}H_{17}O_4Cl$ | 60.71 | 5.77 |

Example 11

A glass vessel was charged with 248 mg of the spiro[1,5-dihydro-2,4-benzodioxepin-4'-methylene-3,2'-[1,3]dioxepane] obtained in Example 8 and 2.7 mg of t-butyl hydroperoxide. The contents were degassed and the vessel was sealed. The vessel and the contents were heated at 180° C. for 20 hours, to give a pale yellow transparent solid. The solid thus obtained was dissolved in 2 ml of methylene chloride and reprecipitated from 50 ml of n-hexane, to give 220 mg of a white solid. The product obtained had a number average molecular weight of 1,780 and a molecular weight distribution of 1.93.

The product was measured for IR spectrum, which showed an absorption at 1,753 $cm^{-1}$ originating from the carbonate of a ring-opened polymer and one at 1,720 $cm^{-1}$ originating from the ketone of the ring-opened polymer.

The product had a density of 1.240 $g/cm^3$, from which the expansion in volume is calculated, based on the monomer density, to be 7.5%.

Example 12

Example 11 was repeated except for using, instead of 248 mg of spiro[1,5-dihydro-4'-methylene-2,4-benzodioxepin-3,2'-[1,3]dioxepane], 282 mg of the spiro[7-chloro-1,5-dihydro-2,4-benzodioxepin-4'-methylene-3,2'-[1,3]dioxepane] obtained in Example 9, to conduct polymerization and obtain a polymer having a number average molecular weight of 1,650 and a molecular weight distribution of 1.90. The expansion in volume based on the monomer density was 8.0%.

Example 13

Example 11 was repeated except for using, instead of 248 mg of spiro[1,5-dihydro-2,4-benzodioxepin-4'-methylene-3,2'-[1,3]dioxepane], 296 mg of the spiro[7-chloro-1,5-dihydro-2,4-benzodioxepin-4'-methylene-5'-methyl-3,2'-[1,3]dioxepane] obtained in Example 10, to conduct polymerization and obtain a polymer having a number average molecular weight of 2,040 and a molecular weight distribution of 2.20. The expansion in volume based on the monomer density was 8.3%.

Example 14

Example 11 was repeated except for using, instead of 248 mg of spiro[1,5-dihydro-2,4-benzodioxepin-4'-methylene-3,2'-[1,3]dioxepane], a mixture of 124 mg of the spiro[1,5-dihydro-2,4-benzodioxepin-4'-methylene-3,2'-[1,3]dioxepane] and 50 mg of methyl methacrylate, to conduct polymerization and obtain a polymer having a number average molecular weight of 4,500 and a molecular weight distribution of 1.87. The expansion in volume based on the monomer density was −0.6%.

Example 15

Figure 13:
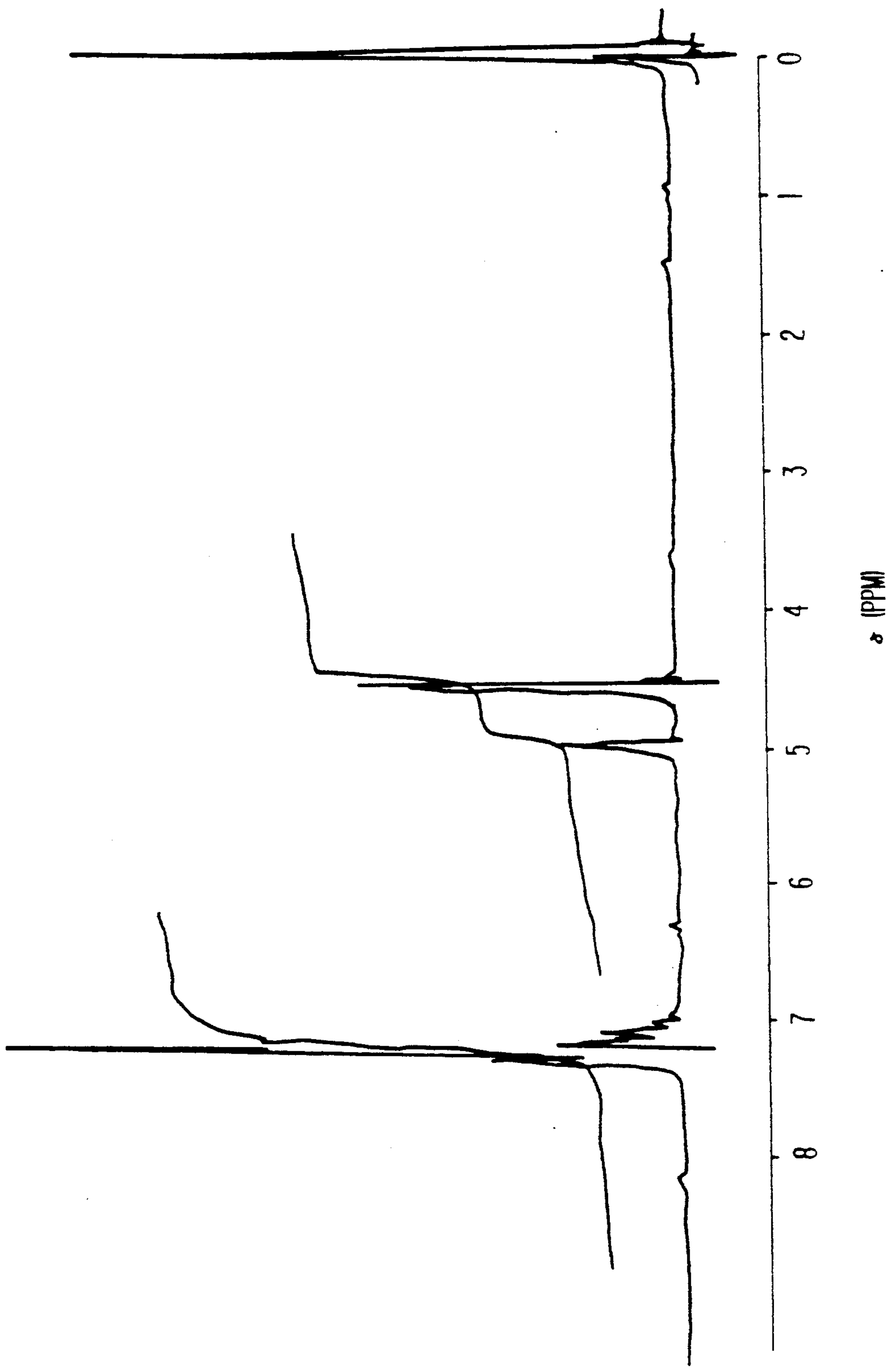
FIGS. 13 and 14 show an $^1$H-NMR spectrum and an IR spectrum of the dioxane produced as an intermediate in Example 15, respectively.

The air inside a 200-ml glass vessel equipped with a stirrer was fully replaced by dry nitrogen gas. The vessel was then charged with 9.69 g (110 mmoles) of 2-methylene-1,3-propanediol, 20.2 g (200 mmoles) of triethylamine and 50 ml of dry methylene chloride. To the mixture, a solution of 26.9 g (100 mmoles) of dichlorodiphenoxymethane in 50 ml of dry methylene chloride was added with stirring at a room temperature over 2 hours. After being stirred at a room temperature for 20 hours, the mixture was washed twice with 50 ml of water and the organic layer was separated from water layer. The organic layer was dried over anhydrous sodium sulfate, concentrated and then distilled under reduced pressure, to give 18.3 g of a colorless transparent liquid. The liquid thus obtained was identified by $^1H$-NMR spectrometry and IR spectrometry to be 2,2-diphenoxy-5-methylene-1,3-dioxane. The yield was 64%. $^1H$-NMR—the spectrum is shown in FIG. 13.

Solvent: deuterated chloroform

Internal standard reference: tetramethylsilane

TABLE 13

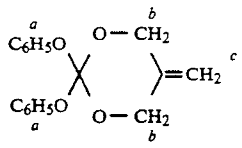

| | δ (ppm) | Peak area ratio | Multiplicity |
|---|---|---|---|
| b | 4.50 to 4.65 | 4H | multiplet |
| c | 4.96 to 5.08 | 2H | multiplet |
| a | 6.90 to 7.40 | 10H | multiplet |

Figure 14:
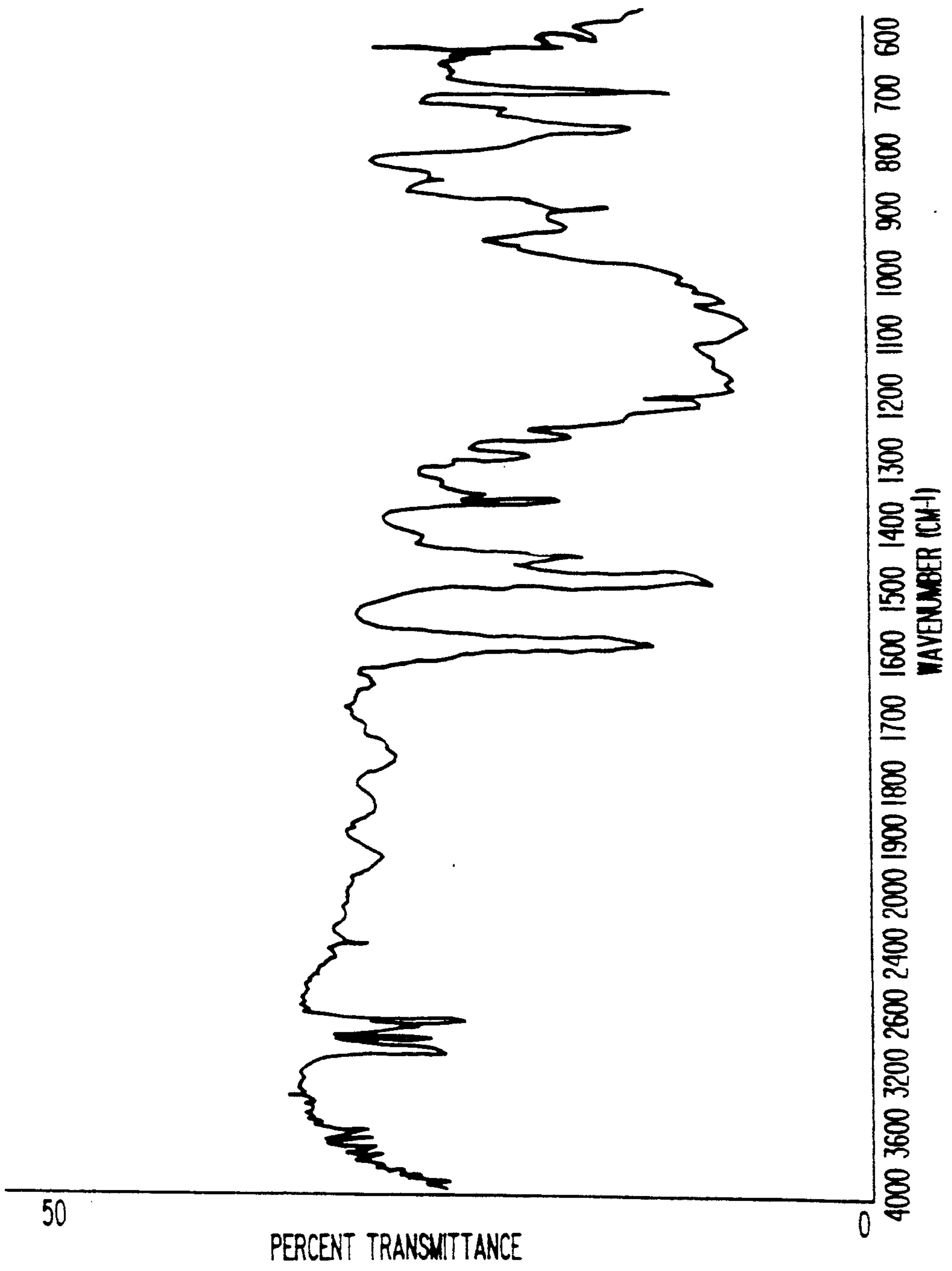

The IR spectrum is shown in FIG. 14.

The air inside a 200-ml glass vessel equipped with a stirrer was fully replaced by dry nitrogen gas. The vessel was then charged with 14.2 g (50 mmoles) of the 2,2-diphenoxy-5-methylene-1,3-dioxane obtained in the above reaction, 429 mg (2.25 mmoles) of p-toluenesulfonic acid monohydrate and 60 ml of dry methylene chloride. To the mixture, 6.91 g (50 mmoles) of o-xylylene glycol Was added at a room temperature. After being stirred at a room temperature for 70 hours, the mixture was washed three times with 60 ml of 1N sodium hydroxide solution. The organic layer was separated from water layer, dried over anhydrous sodium sulfate, and then concentrated, whereby white solid precipitated. The white solid was purified by recrystallization from a 1/1 by volume mixed solvent of n-hexane/ethyl acetate, to give 7.03 g of colorless crystal. The crystal thus obtained was identified by $^1$H-NMR spectrometry and IR spectrometry to be spiro[1,5-dihydro-2,4-benzodioxepin-5'-methylene-3,2'-[1,3]dioxane]. The yield was 60%.

Figure 15:
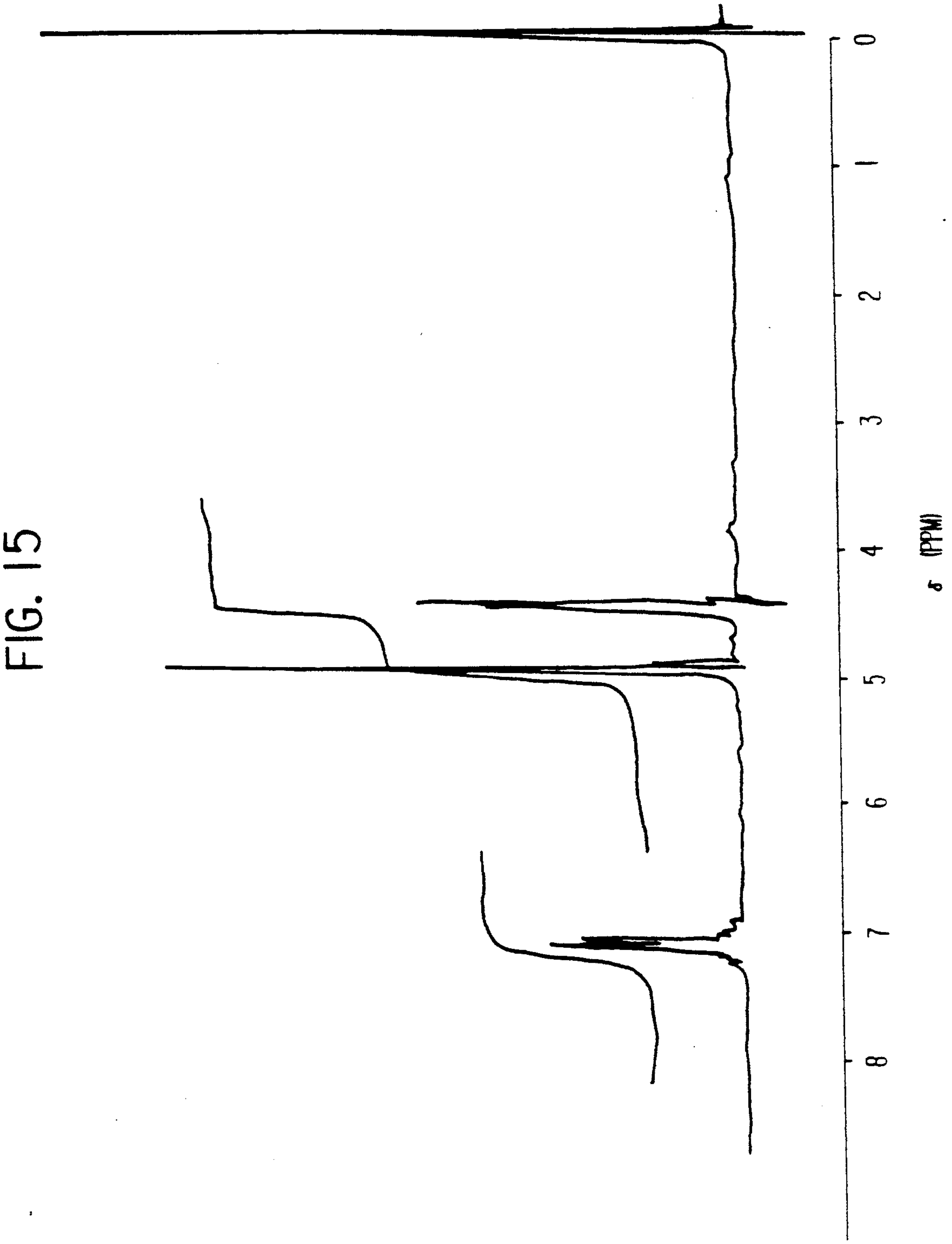
FIGS. 15 and 16 show an $^1$H-NMR spectrum and an IR spectrum of the spiroorthocarbonate obtained in Example 15, respectively.

$^1$H-NMR—the spectrum is shown in FIG. 15.

Solvent: deuterated chloroform

Internal standard reference: tetramethylsilane

TABLE 15

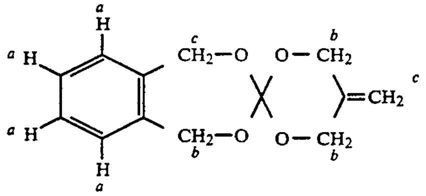

| | δ (ppm) | Peak area ratio | Multiplicity |
|---|---|---|---|
| b | 4.36 to 4.50 | 4H | multiplet |
| c | 4.83 to 5.05 | 6H | multiplet |
| a | 6.85 to 7.27 | 4H | multiplet |

Figure 16:
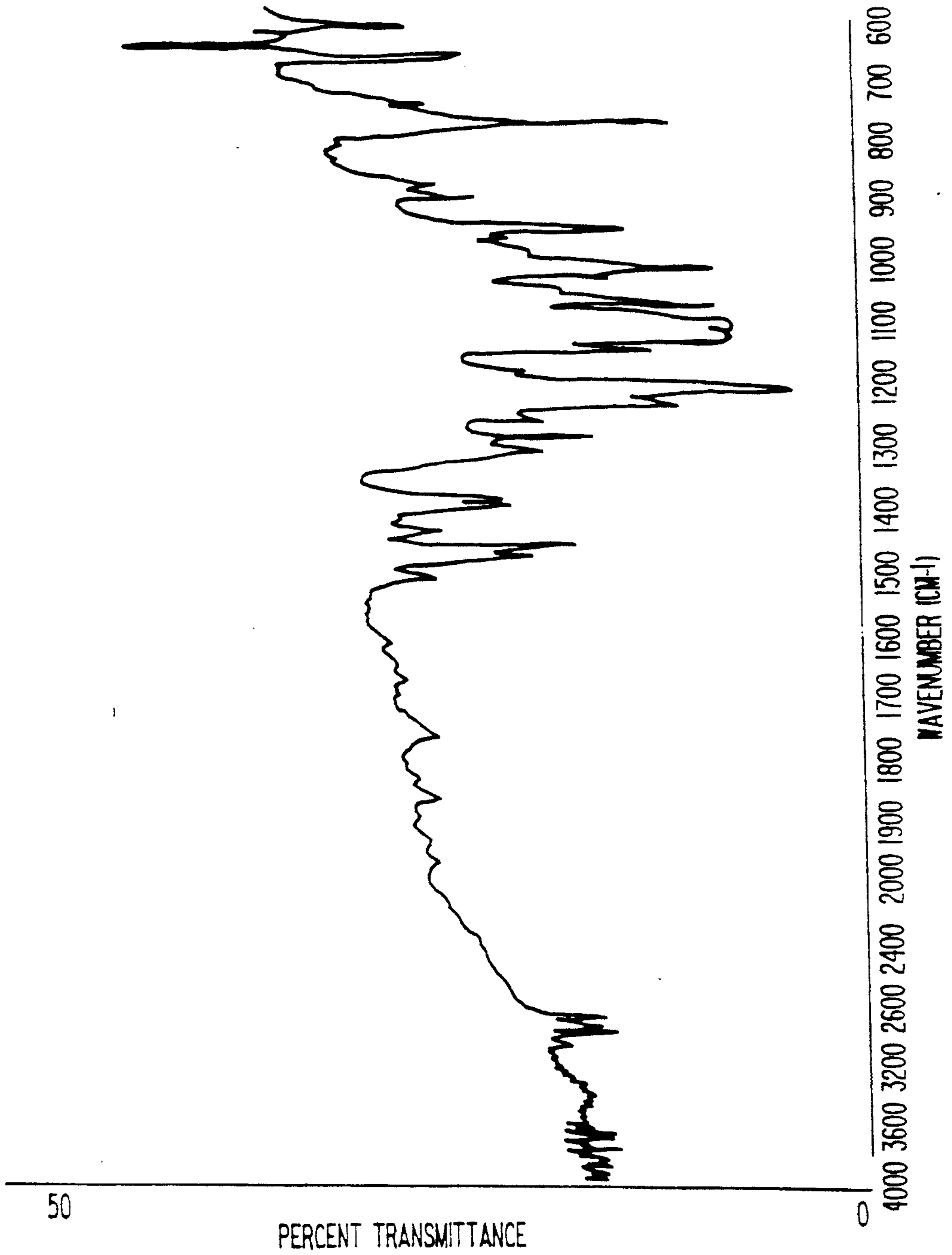

The IR spectrum is shown in FIG. 16.

Density: 1.320

Example 16

Example. 15 was repeated except for using 12.76 g (110 mmoles) of 1,3-dimethyl-2-methylene-1,3-propanediol instead of 9.69 g (110 mmoles) of 2-methylene-1,3-propanediol, to obtain 7 32 g of spiro[1,5-dihydro-2,4-benzodioxepin-4',6'-dimethyl-5'-methylene-3,2'-[1,3]dioxane].

TABLE 16

| Elemental analysis | C % | H % |
|---|---|---|
| Observed | 68.84 | 7.03 |
| Calculated as $C_{15}H_{18}O_4$ | 68.69 | 6.92 |

Example 17

Example 15 was repeated except for using 12.76 g (110 mmoles) of 1,3-dimethyl-2-methylene-1,3-propanediol and 8.62 g (50 mmoles) of 4-chloro-o-xylylene glycol, instead of 9.69 g (110 mmoles) of 2-methylene-1,3-propanediol and 6.91 g (50 mmoles) of o-xylylene glycol respectively, to obtain 8.34 g of spiro[7-chloro-1,5-dihydro-2,4-benzodioxepin-4'6'-dimethyl-5'-methylene-3,2'-[1,3]dioxane].

TABLE 17

| Elemental analysis | C % | H % |
|---|---|---|
| Observed | 60.99 | 5.48 |
| Calculated as $C_{15}H_{17}O_4Cl$ | 60.71 | 5.77 |

Example 18

A glass vessel was charged with 234 mg of the spiro[1,5-dihydro-2,4-benzodioxepin-5'-methylene-3,2'-[1,3]dioxane] obtained in Example 15 and 2.7 mg of t-butyl hydroperoxide. The contents were degassed and the vessel was sealed. The vessel and the contents were heated at 180° C. for 20 hours, to give a light yellow transparent solid. The solid thus obtained was dissolved in 2 ml of methylene chloride and reprecipitated from 50 ml of n-hexane. to give 211 mg of a white solid. The product obtained had a number average molecular weight of 1,540 and a molecular weight distribution of 1.78.

The product was measured for IR spectrum, which showed an absorption at 1,753 $cm^{-1}$ originating from the carbonate of a ring-opened polymer.

The product had a density of 1.272 g/cm$^3$, from which the expansion in volume is calculated, based on the monomer density, to be 3.6%.

Example 19

Example 18 was repeated except for using, instead of 234 mg of spiro[1,5-dihydro-2,4-benzodioxepin-5'-methylene-3,2'-[1,3]dioxane], 262 mg of the spiro[1,5-dihydro-2,4-benzodioxepin-4',6'-dimethyl-5'-methylene-3,2'-[1,3]dioxane] obtained in Example 16, to conduct polymerization and obtain a polymer having a number average molecular weight of 2,980 and a molecular Weight distribution of 1.63. The expansion in volume based on the monomer density was 4.4%.

Example 20

Example 18 was repeated except for using, instead of 234 mg of spiro[1,5-dihydro-2,4-benzodioxepin-5'-methylene 3,2'-[1,3]dioxane], 297 mg of the spiro[7-chloro-1,5-dihydro-2,4-benzodioxepin-4'6'-dimethyl-5'-methylene-3,2'-[1,3]dioxane] obtained in Example 17, to conduct polymerization and obtain a polymer having a number average molecular weight of 2,240-and a molecular weight distribution of 1.89. The expansion in volume based on the monomer density was 4.9%.

Example 21

Example 18 was repeated except for using, instead of 234 mg of spiro[1,5-dihydro-2,4-benzodioxepin-5'-methylene-3,2'-[1,3]dioxane], a mixture of 117 mg of spiro[1,5-dihydro-2,4-benzodioxepin-5'-methylene-3,2'-[1,3]dioxane] and 50 mg of methyl methacrylate, to conduct polymerization and obtain a polymer having a number average molecular weight of 3,390 and a molecular weight distribution of 2.04. The expansion in volume based on the monomer density was −1.1%.

Example 22

The air inside a 200-ml glass vessel equipped with a stirrer was fully replaced by dry nitrogen gas. The vessel was then charged with 10.2 g (100 mmoles) of 2-methylene-1,4-butanediol, 20.2 g (200 mmoles) of triethylamine and 50 ml of dry methylene chloride. To the mixture, a solution of 26.91 g (100 mmoles) of dichlorodiphenoxymethane in 25 ml of dry methylene chloride was added with ice-cooling over 40 minutes. After being stirred at a room temperature for 13 hours, the mixture was washed twice with 100 ml of water and the organic layer was separated from water layer. The organic layer was dried over anhydrous sodium sulfate, concentrated and then distilled under reduced pressure, to give 20.40 g of a colorless transparent liquid boiling at 158 to 61° C./0.3 mmHg. The liquid thus obtained was identified by $^1$H-NMR spectrometry and IR spectrometry to be 2,2-diphenoxy-5-methylene-1,3-dioxepane. The yield was 68%.

Figure 17:
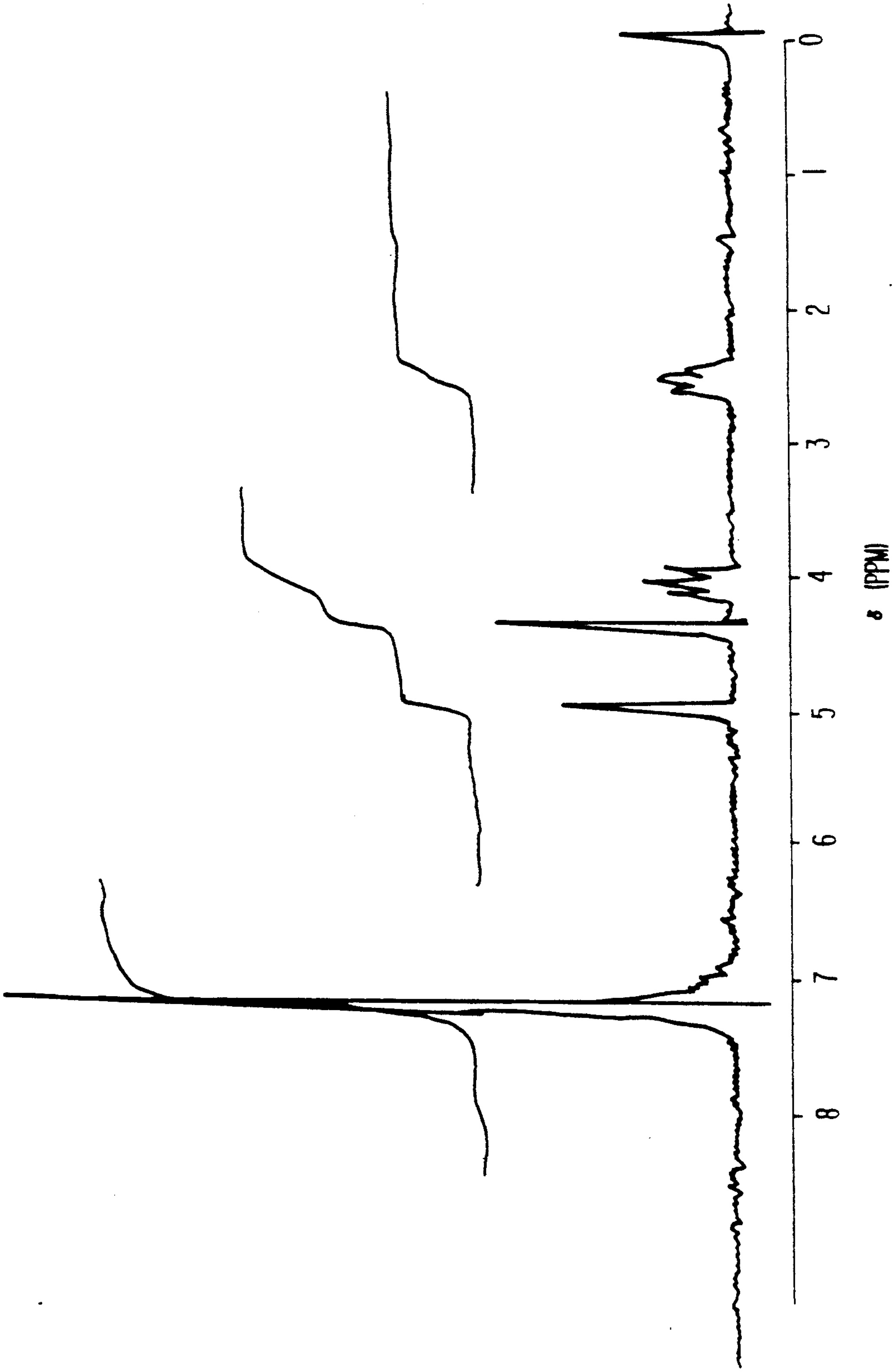
FIGS. 17 and 18 show an $^1$H-NMR spectrum and an IR spectrum of the dioxepane produced as an intermediate in Example 22, respectively.

$^1$H-NMR—the spectrum is shown in FIG. 17.
Solvent: deuterated chloroform
Internal standard reference: tetramethylsilane

TABLE 18

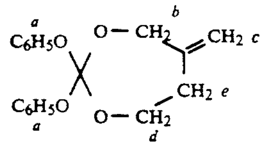

| | δ (ppm) | Peak area ratio | Multiplicity |
|---|---|---|---|
| e | 2.53 | 2H | triplet |
| d | 4.03 | 2H | triplet |
| b | 4.38 | 2H | singlet |
| c | 5.00 | 2H | singlet |
| a | 6.87 to 7.22 | 10H | multiplet |

Figure 18:
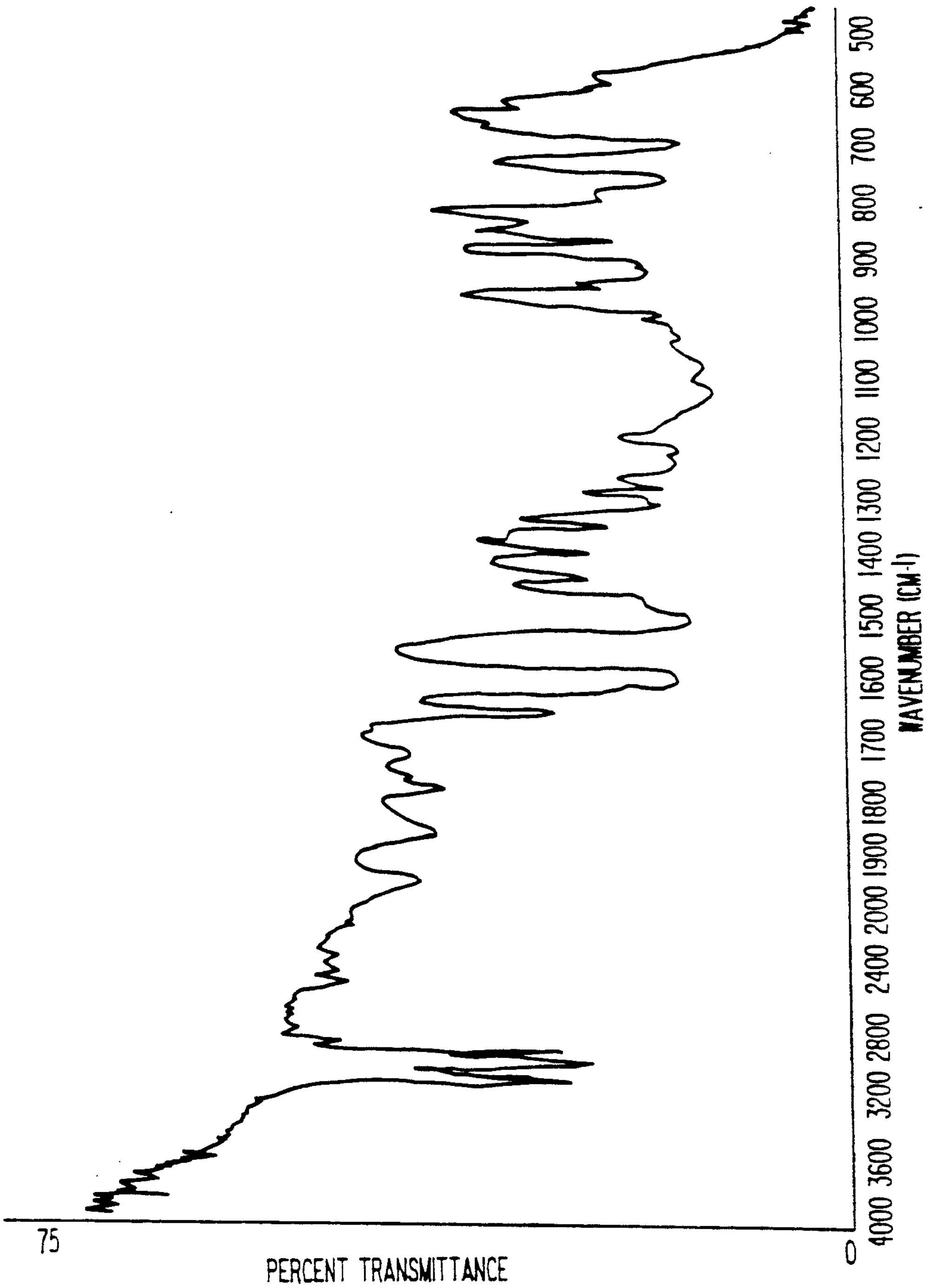

The IR spectrum is shown in FIG. 18.

The air inside a 200-ml glass vessel equipped with a stirrer was fully replaced by dry nitrogen gas. The vessel was then charged with 10.44 g (35 mmoles) of the 2,2-diphenoxy-5-methylene-1,3-dioxepane obtained in the above reaction, 270 mg (1.41 mmoles) of p-toluenesulfonic acid monohydrate and 40 ml of dry methylene chloride. To the mixture, 4.84 g (35 mmoles) of o-xylylene glycol was added at a room temperature. After being stirred at a room temperature for 18 hours, the mixture was washed three times with 40 ml of 1N sodium hydroxide solution. The organic layer was separated from water layer, dried over anhydrous sodium sulfate, and then concentrated, whereby white solid precipitated. The white solid was purified by recrystallization from a 1/1 by volume mixed solvent of n-hexane/ethyl acetate, to give 7.39 g of colorless crystal. The crystal thus obtained was identified by $^1$H-NMR spectrometry and IR spectrometry to be spiro[1,5-dihydro-2,4-benzodioxepin-5'-methylene-3,2'-[1,3]dioxepane]. The yield was 85%.

TABLE 19

| Elemental analysis | C % | H % |
|---|---|---|
| Observed | 67.43 | 6.61 |
| Calculated as $C_{14}H_{16}O_4$ | 67.73 | 6.50 |

Figure 19:
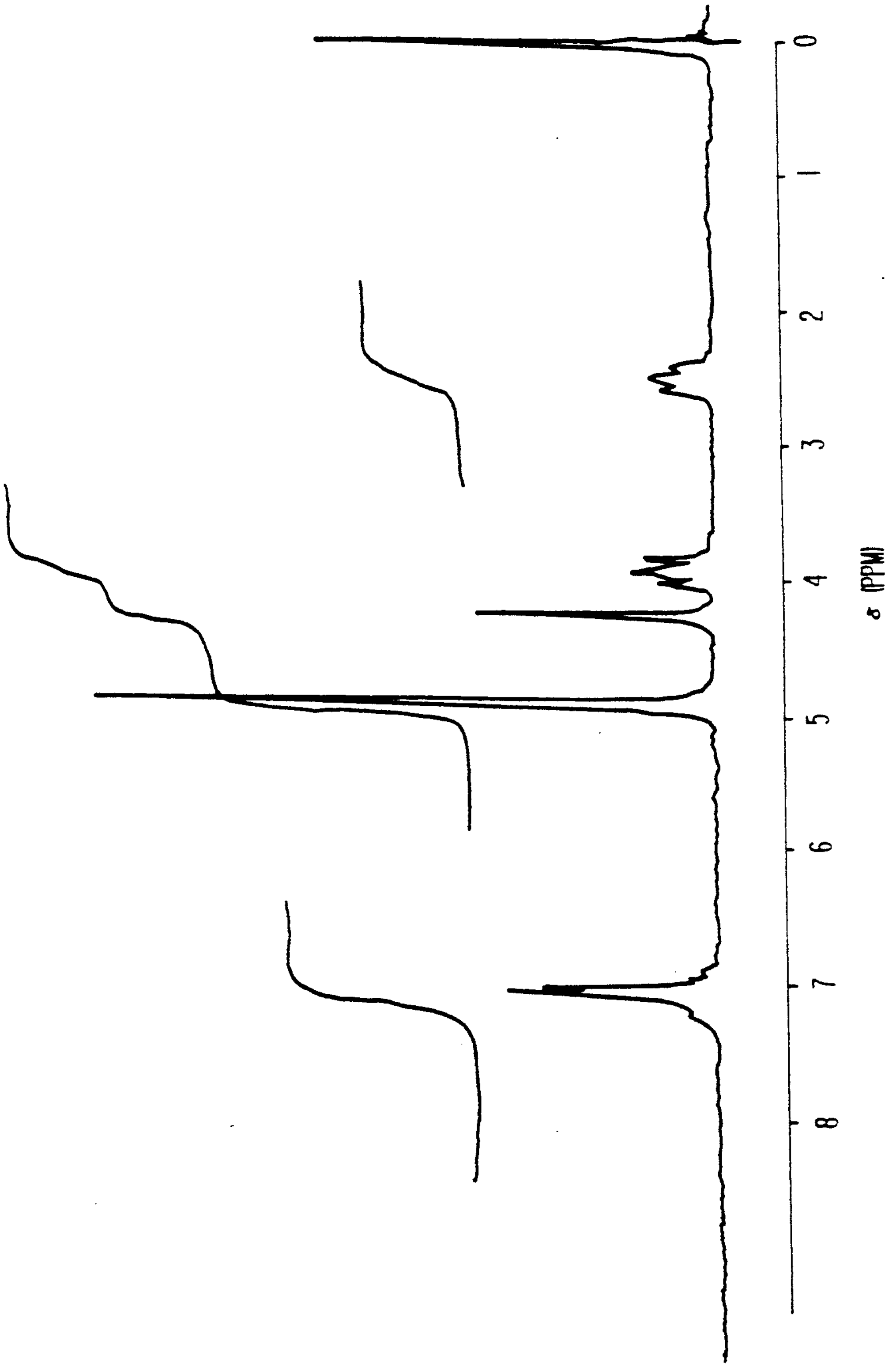
FIGS. 19 and 20 show an $^1$H-NMR spectrum and a IR spectrum of the-spiroorthocarbonate obtained in Example 22, respectively.

Melting point: 114° to 116° C.
$^1$H-NMR—the spectrum is shown in FIG. 19.
Solvent: deuterated chloroform
Internal standard reference: tetramethylsilane

TABLE 20

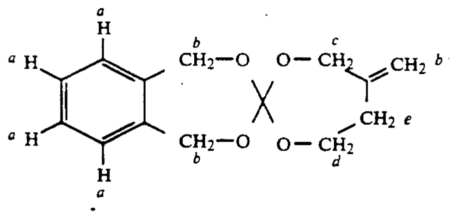

| | δ (ppm) | Peak area ratio | Multiplicity |
|---|---|---|---|
| e | 2.48 | 2H | triplet |
| d | 3.90 | 2H | triplet |
| c | 4.25 | 2H | singlet |
| b | 4.95 | 6H | singlet |

TABLE 20-continued

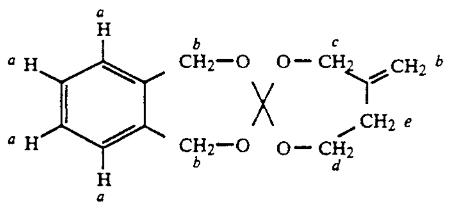

| | δ (ppm) | Peak area ratio | Multiplicity |
|---|---|---|---|
| a | 6.83 to 7.40 | 4H | multiplet |

Figure 20:
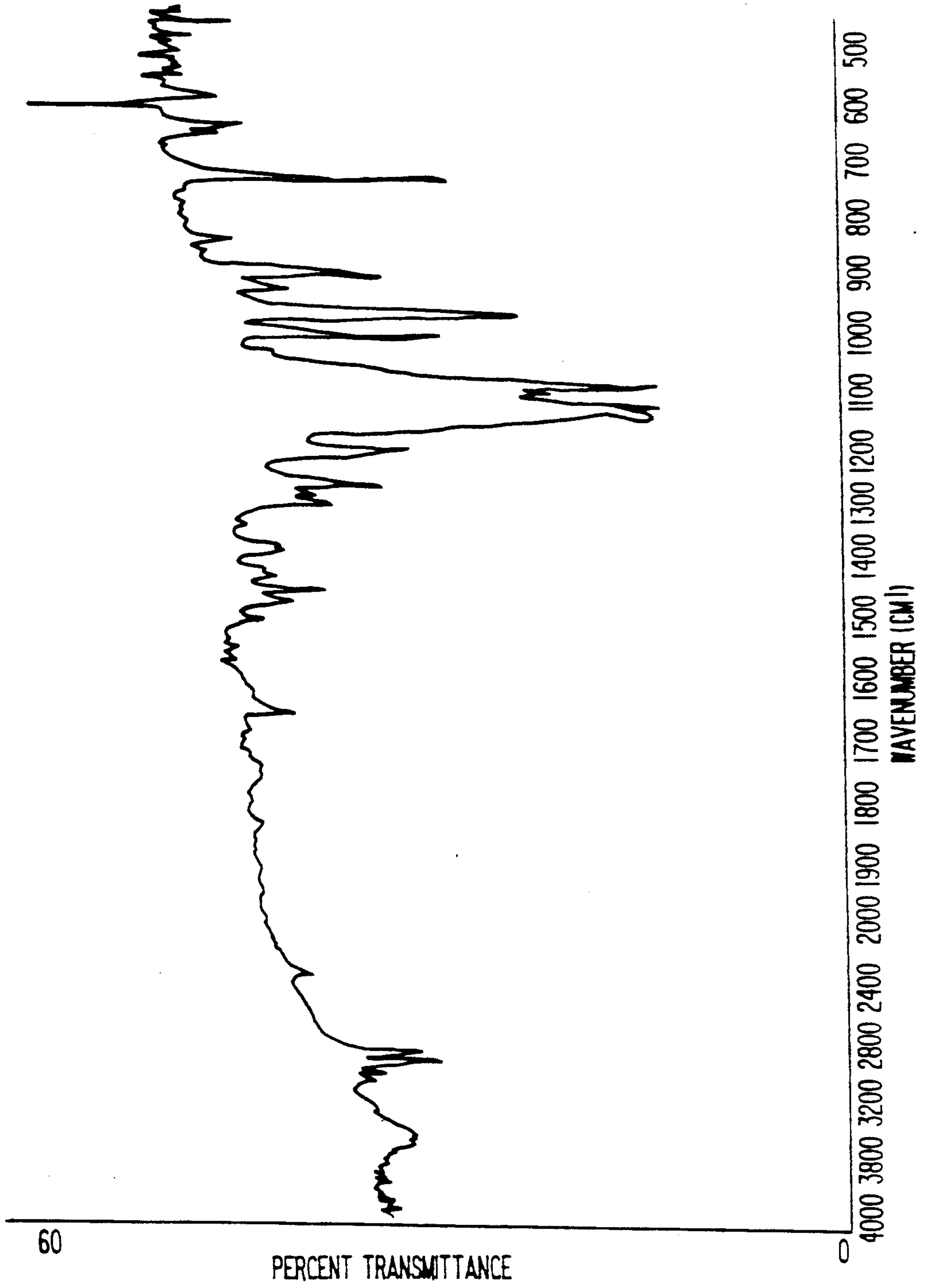

The IR spectrum is shown in FIG. 20. Density: 1.318

Example 23

Example 22 was repeated except for using 14.4 g (100 mmoles) of 1,3,4-trimethyl-2-methylene-1,4-butanediol instead of 10.2 g (100 mmoles) of 2-methylene-1,4-butanediol, to obtain 6.31 g of spiro[1,5-dihydro-2,4-benzodioxepin-5'-methylene-4',6',7'-trimethyl-3,2'-[1,3]dioxepane].

TABLE 21

| Elemental analysis | C % | H % |
|---|---|---|
| Observed | 70.11 | 7.77 |
| Calculated as $C_{17}H_{22}O_4$ | 70.32 | 7.64 |

Example 24

Example 22 was repeated except for using 6.04 g (35 mmoles) of 4-chloro-o-xylylene glycol, instead of 4.84 g (35 mmoles) of o-xylylene glycol, to obtain 7.90 g of spiro[7-chloro-1,5-dihydro-2,4-benzodioxepin-5'-methylene-3,2'-[1,3]dioxepane].

TABLE 22

| Elemental analysis | C % | H % |
|---|---|---|
| Observed | 59.33 | 5.45 |
| Calculated as $C_{14}H_{16}O_4Cl$ | 59.48 | 5.34 |

Example 25

A glass vessel was charged with 248 mg of the spiro[1,5-dihydro-2,4-benzodioxepin-5'-methylene-3,2'-[1,3]dioxepane] obtained in Example 22 and 2.7 mg of t-butyl hydroperoxide. The contents were degassed and the vessel was sealed. The vessel and the contents Were heated at 180° C. for 4 hours, to give a pale yellow transparent solid. The solid thus obtained was dissolved in 2 ml of methylene chloride and reprecipitated from 50 ml of n-hexane, to give 50 mg of a transparent liquid. The product obtained had a number average molecular weight of 1,380 and a molecular weight distribution of 1.97.

The product was measured for IR spectrum, which showed an absorption at 1,753 $cm^{-1}$ originating from the carbonate of a ring-opened polymer.

The product had a density of 1.259 g/$cm^3$, from which the expansion in volume is calculated, based on the monomer density, to be 4.5%.

Example 26

Example 25 was repeated except for using, instead of 248 mg of spiro[1,5-dihydro-2,4-benzodioxepin-5'- methylene-3,2'-[1,3]dioxepane], 290 mg of the spiro[1,5-dihydro-2,4-benzodioxepin-5'-methylene-4',6',7'-trimethyl-3,2'-[1,3]-dioxepane] obtained in Example 23, to conduct polymerization and obtain a polymer having a number average molecular weight of 1,540 and a molecular weight distribution of 1.88. The expansion in volume based on the monomer density was 4.7%.

Example 27

Example 25 was repeated except for using, instead of 248 mg of spiro[1,5-dihydro-2,4-benzodioxepin-5'-methylene-3,2'-[1,3]dioxepane], 283 mg of the spiro[7-chloro-1,5-dihydro-2,4-benzodioxepin-5'-methylene-3,2'-[1,3]dioxepane] obtained in Example 24, to conduct polymerization and obtain a polymer having a number average molecular weight of 2,010 and a molecular weight distribution of 2.01. The expansion in volume based on the monomer density was 5.1%.

Example 28

Example 25 was repeated except for using, instead of 248 mg of spiro[1,5-dihydro-2,4-benzodioxepin-5'-methylene-3,2'-[1,3]dioxepane], a mixture of 124 mg of spiro[1,5-dihydro-2,4-benzodioxepin5'-methylene--3,2'-[1,3]dioxepane] and 50 mg of methyl methacrylate, to conduct polymerization and obtain a polymer having a number average molecular weight of 3,670 and a molecular weight distribution of 1.99. The expansion in volume based on the monomer density was −1.5%.

Example 29

A glass vessel is charged with a spiroorthocarbonate, a sulfonium salt, a vinyl monomer, an initiator and a solvent, as shown in Table 23, in amounts as shown. The contents are degassed and then the vessel is sealed. The vessel and contents are heated under a condition as shown in Table 23, to give a pale yellow transparent liquid. The liquid obtained is reprecipitated from methanol, to give a pale yellow solid.

IR spectrometry on the obtained solid reveals that an absorption at 1695 $cm^{-1}$ originating from $C{=}CH_2$ have disappeared and that there are observed absorptions at 1217, 1167 and 1076 $cm^{-1}$ originating from C—O—C. $^1H$-NMR spectrometry and elemental analysis on this solid show that it has a structure of

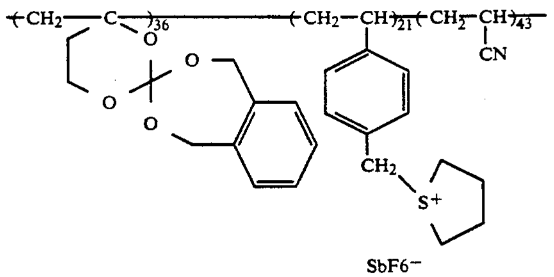

The product is heated under a condition as shown in Table 23, to give a pale yellow crosslinked polymer. The expansion in volume obtained from the density of the cross-linked polymer and that of the solid before crosslinking is 0.7%.

Examples 30 through 40

Example 29 is repeated several times except for changing starting materials and their amounts as shown in Table 23. The obtained curable compositions are heated to be crosslinked. The heating conditions and the results obtained are also shown in Table 23.

Example 41

To a mixture of 0.6 g of spiro[1,5-dihydro-2,4-benzodioxepin-5'-methylene-3,2'-[1,3]dioxepane], 0.2 g of methyl methacrylate, 0.2 g of 2,2-bis[p-(γ-methacryloxy-β-hydroxypropoxy)phenyl]propane and 0.01 g of di-tert-butyl peroxide, was added 3.0 g of quartz powder [average particle diameter 2.4 μm] surface-treated with γ-methacryloxypropyltrimethoxysilane and the resulting mixture was sufficiently mixed to give a dental composition paste. The paste thus obtained was cured at 130° C. for 10 hours in the air to yield a hard solid. The expansion in volume based on the volume of the paste before curing was 0.0%.

Obviously, numerous modifications and variations are possible in light of the above teachings. It is therefore to be understood that within the scope of the appended claims, the invention may be practiced otherwise than as specifically described herein.

TABLE 23

| Example | Monomers fed (mol %) | | | Polymerization conditions | | | | Composition of polymer (mol %) | | | Heating conditions | | | Expansion in volume (%) |
|---|---|---|---|---|---|---|---|---|---|---|---|---|---|---|
| | Spiroortho carbonate | Sulfonium salt | Vinyl monomer | Initiator; mol % based on monomer | Temp. (°C.) | Time (hr) | Solvent | a/ | b/ | c/ | Temp. (°C.) | Time (hr) | Solvent | |
| 29 | IIa (40) | Sa (20) | AN (40) | AIBN (3) | 60 | 20 | — | 36 | 21 | 43 | 120 | 10 | acetonitrile | 0.7 |
| 30 | IIa (45) | Sa (10) | MMA (45) | AIBN (3) | 60 | 24 | — | 32 | 15 | 53 | 120 | 10 | acetonitrile | 0.5 |
| 31 | IIb (40) | Sb (10) | AN (50) | AIBN (1) | 70 | 10 | — | 34 | 14 | 52 | 120 | 10 | — | 0.5 |
| 32 | IXa (40) | Sa (20) | AN (40) | AIBN (1) | 60 | 20 | — | 50 | 29 | 21 | 120 | 10 | DMF | 0.9 |
| 33 | IXb (45) | Sb (10) | AN (45) | AIBN (3) | 60 | 20 | CB | 60 | 28 | 12 | 140 | 5 | DMF | 1.0 |
| 34 | IXa (50) | Sb (20) | MMA (30) | AIBN (1) | 70 | 10 | — | 65 | 23 | 12 | 120 | 10 | — | 1.1 |
| 35 | XIa (40) | Sa (20) | ST (40) | AIBN (3) | 60 | 20 | — | 46 | 27 | 27 | 120 | 10 | acetonitrile | 0.8 |
| 36 | XIa (45) | Sa (10) | AN (45) | AIBN (3) | 60 | 20 | — | 50 | 30 | 20 | 120 | 10 | acetonitrile | 0.3 |
| 37 | XIb (45) | Sb (20) | AN (35) | BPO (3) | 70 | 48 | CB | 54 | 28 | 18 | 120 | 10 | — | 0.5 |
| 38 | XIVa (40) | Sa (20) | AN (40) | AIBN (3) | 60 | 10 | — | 51 | 30 | 19 | 120 | 10 | DMF | 0.8 |
| 39 | XIVa (45) | Sa (10) | MMA (45) | AIBN (1) | 60 | 10 | — | 70 | 25 | 5 | 140 | 5 | — | 0.6 |

TABLE 23-continued

| Ex-ample | Monomers fed (mol %) Spiroortho carbonate | Sulfo-nium salt | Vinyl monomer | Polymerization conditions Initiator; mol % based on monomer | Temp. (°C.) | Time (hr) | Sol-vent | Composition of polymer (mol %) a/ | b/ | c/ | Heating conditions Temp. (°C.) | Time (hr) | Sol-vent | Expansion in volume (%) |
|---|---|---|---|---|---|---|---|---|---|---|---|---|---|---|
| 40 | XIVb (40) | Sb (20) | ST (40) | AIBN (3) | 60 | 10 | DMF | 59 | 28 | 13 | 120 | 10 | — | 0.5 |

Notes:
AN: acrylonitrile, MMA: methyl methacrylate, AIBN: azobisisobutyronitrile, CB: chlorobenzene, DMF: dimethylformamide, BPO: benzoyl peroxide, ST: styrene
Coding for the spiroorthocarbonates and sulfonium salts used are as shown on the next page.

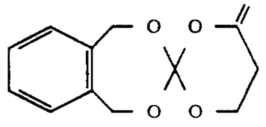
IIa

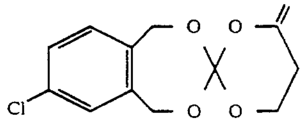
IIb

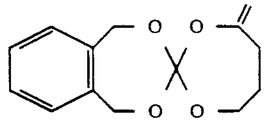
IXa

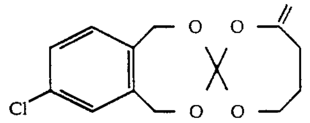
IXb

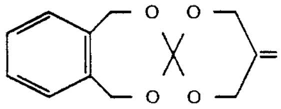
XIa

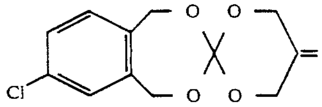
XIb

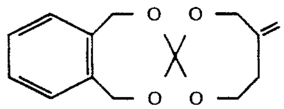
XIVa

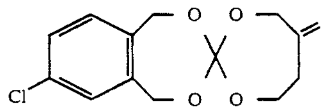
XIVb

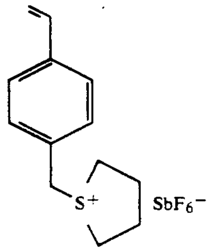
Sa

-continued

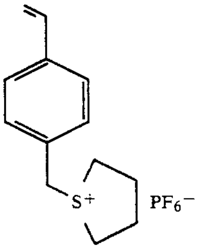
Sb

What is claimed is:

1. A polymerizable composition comprising an asymmetric spiroorthocarbonate compound having only one exomethylene group and represented by the following formula (1)

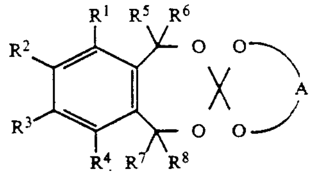
(1)

wherein A is selected from the group consisting of:

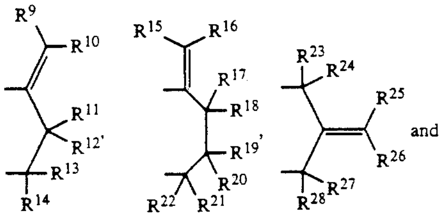
and

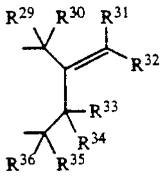

wherein $R^1$, $R^2$, $R^3$ and $R^4$ are each hydrogen, lower alkyl having not more than 8 carbon atoms, alkoxy, halogen, nitro, cyano, amino, amide, hydroxyl or alkyl ester having not more than 20 carbon atoms, and $R^5$, $R^6$, $R^7$ and $R^8$, $R^9$ through $R^{14}$, $R^{15}$ through $R^{22}$, $R^{23}$ through $R^{28}$ and $R^{29}$ through $R^{36}$ are each hydrogen or a lower alkyl having not more than 8 carbon atoms and a polymerization catalyst selected from the group consisting of a cationic polymerization catalyst and a radical polymerization catalyst.

2. A polymerizable composition according to claim 1, further comprising an ethylenic monomer.

3. The composition of claim 1, wherein A of the formula (1) is

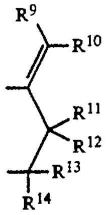

or

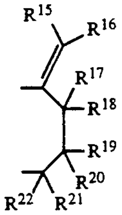

wherein $R^9$-$R^{22}$ are as defined above, and the exomethylene group is present at the α-position of the ether oxygen.

4. The composition of claim 1, wherein A of the formula (1) is

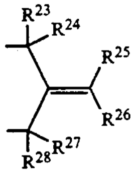

or

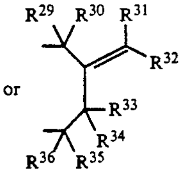

wherein $R^{23}$-$R^{36}$ are as defined above, and the exomethylene group is present at the β-position of the ether oxygen.

5. The composition of claim 1, wherein said polymerization catalyst is a cationic polymerization catalyst.

6. The composition of claim 1, wherein said polymerization catalyst is a radical polymerization catalyst.

7. The composition of claim 2, wherein said ethylenic monomer is selected from the group consisting of (meth)acrylic acid, (meth)acrylates, acrylonitrile, acrylamide, vinyl chloride, vinyl acetate and styrene.

* * * * *

UNITED STATES PATENT AND TRADEMARK OFFICE

CERTIFICATE OF CORRECTION

PATENT NO. : 5,298,631

DATED : March 29, 1994

INVENTOR(S) : Fumio SANDA, et al.

It is certified that error appears in the above-indentified patent and that said Letters Patent is hereby corrected as shown below:

On the title page, Item [30], the 1st and 2nd Foreign Application Priority Data should read as follows:

--Mar. 12, 1991 [JP] Japan ............. 3-74154
Mar. 12, 1991 [JP] Japan ............. 3-74155--

Signed and Sealed this

Twenty-third Day of August, 1994

Attest:

BRUCE LEHMAN

*Attesting Officer* *Commissioner of Patents and Trademarks*